US012573113B2

(12) United States Patent

Mikhail et al.

(10) Patent No.: US 12,573,113 B2
(45) Date of Patent: Mar. 10, 2026

(54) SYSTEM AND METHOD FOR DISPLAYING THE LOCATION OF A FERROMAGNETIC OBJECT IN A LIVING ORGANISM

(71) Applicants: Albert A. Mikhail, Sherman Oaks, CA (US); Amgad Barsom, La Canada Flintridge, CA (US); Elias Bachaalany, Halat (LB); Imad Maalouf, El Metn (LB); Pierre Touma, Austin, TX (US)

(72) Inventors: Albert A. Mikhail, Sherman Oaks, CA (US); Amgad Barsom, La Canada Flintridge, CA (US); Elias Bachaalany, Halat (LB); Imad Maalouf, El Metn (LB); Pierre Touma, Austin, TX (US)

( * ) Notice: Subject to any disclaimer, the term of this patent is extended or adjusted under 35 U.S.C. 154(b) by 133 days.

(21) Appl. No.: 18/225,108

(22) Filed: Jul. 22, 2023

(65) Prior Publication Data

US 2024/0005568 A1     Jan. 4, 2024

Related U.S. Application Data

(63) Continuation-in-part of application No. 16/947,890, filed on Aug. 23, 2020, now Pat. No. 11,759,117.

(51) Int. Cl.
G06T 11/00     (2006.01)
A61B 5/00     (2006.01)
(Continued)

(52) U.S. Cl.
CPC ............ G06T 11/003 (2013.01); A61B 5/062 (2013.01); A61B 5/743 (2013.01); A61B 34/25 (2016.02);
(Continued)

(58) Field of Classification Search
None
See application file for complete search history.

(56) References Cited

U.S. PATENT DOCUMENTS

| | | |
|---|---|---|
| 2,321,355 A | 6/1943 | Berman |
| 2,321,356 A | 6/1943 | Berman |

(Continued)

FOREIGN PATENT DOCUMENTS

| | | |
|---|---|---|
| GB | 1283521 | 7/1972 |

OTHER PUBLICATIONS

Peleg et al., "Implementing metal detector technology and a navigation system in the removal of shrapnel," (Jan. 30, 2009), Computer Aided Surgery, vol. 14, 2009—Issue 1-3.. (Year: 2009) (Year: 2009).*

(Continued)

*Primary Examiner* — Keith M Raymond
*Assistant Examiner* — Ashish S Jasani

(57) ABSTRACT

Described is a system and/or method for displaying the location of a ferromagnetic object in a living organism by using a surgical probe. The surgical probe has a shaft with three-dimensional magnetoresistance sensors located on a distal end configured for insertion into the living organism and three-dimensional magnetoresistance sensors located on a proximal end that stays outside of the living organism. The system comprises a display configured to show the relative location of a detected ferromagnetic object to the tip of the probe in a simulated three-dimensional view on a two-dimensional display.

20 Claims, 16 Drawing Sheets

(51) Int. Cl.

| | |
|---|---|
| *A61B 5/06* | (2006.01) |
| *A61B 34/00* | (2016.01) |
| *G01R 33/02* | (2006.01) |
| *G01R 33/09* | (2006.01) |
| *G06F 3/01* | (2006.01) |

(52) U.S. Cl.

CPC ......... *G01R 33/0206* (2013.01); *G01R 33/09* (2013.01); *G06F 3/016* (2013.01); *A61B 2562/0223* (2013.01); *G06T 2211/448* (2023.08)

(56) References Cited

U.S. PATENT DOCUMENTS

| | | | |
|---|---|---|---|
| 2,393,717 | A | 1/1946 | Speaker |
| 2,442,805 | A | 6/1948 | Gilson |
| 2,706,979 | A | 4/1955 | Wallace |
| 3,422,816 | A | 1/1969 | Robinson et al. |
| 3,460,528 | A | 8/1969 | Carney |
| 3,587,583 | A | 6/1971 | Geenberg |
| 4,526,177 | A | 7/1985 | Rudy et al. |
| 4,943,770 | A | 7/1990 | Ashley-Rollman et al. |
| 5,494,035 | A | 2/1996 | Leuthold et al. |
| 5,649,546 | A | 7/1997 | Steinbeck |
| 6,129,668 | A | 10/2000 | Haynor et al. |
| 6,496,713 | B2 | 12/2002 | Avrin et al. |
| 7,525,309 | B2 | 4/2009 | Sherman et al. |
| 9,155,490 | B2 | 10/2015 | Rapoport |
| 10,881,323 | B1 * | 1/2021 | Clauson ............. G01R 33/0005 |
| 10,898,105 | B2 | 1/2021 | Weprin et al. |
| 11,291,384 | B2 | 4/2022 | Ravi et al. |
| 2007/0015960 | A1 | 1/2007 | Gomert et al. |
| 2008/0052932 | A1 | 3/2008 | Xue et al. |
| 2008/0294036 | A1 | 11/2008 | Hoi et al. |
| 2009/0137900 | A1 | 5/2009 | Bonner et al. |
| 2012/0130164 | A1 | 5/2012 | Palese et al. |
| 2013/0184608 | A1 * | 7/2013 | Pezzi ...................... A61M 1/73 |
| | | | 600/11 |
| 2013/0207648 | A1 | 8/2013 | Zibold et al. |
| 2013/0300402 | A1 | 11/2013 | Llu et al. |
| 2016/0029998 | A1 | 2/2016 | Brister et al. |
| 2016/0051164 | A1 * | 2/2016 | Derichs ................... G01R 33/02 |
| | | | 324/226 |
| 2019/0192044 | A1 * | 6/2019 | Ravi ...................... A61B 5/062 |
| 2019/0328217 | A1 | 10/2019 | Moreau et al. |
| 2019/0328245 | A1 | 10/2019 | Albu et al. |
| 2021/0093223 | A1 * | 4/2021 | Kosel ................... A61B 5/6852 |
| 2022/0323160 | A1 * | 10/2022 | Martens .............. A61B 5/7405 |

OTHER PUBLICATIONS

Asahi Kasei Microdevices Datasheet for AK09940 ultrahigh precision 3-axis electronic magnetometer.

Richardo Ferreira, Elvira Pa, Paulo Freintas, Joao Roberir, Jose Germano and Leonel Sousa. 2-Axis Magnetometers Based on Full Wheatstone Bridges Incorporating Magnetic Tunnel Junctions Connected in Series. Published in IEEE Transactions on Magnetics, Nov. 2012.

* cited by examiner

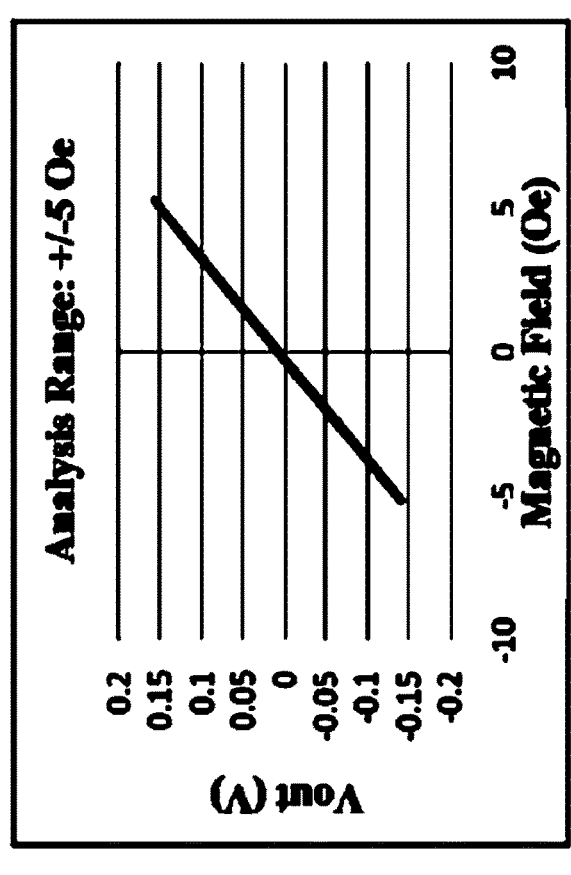
FIG. 4B
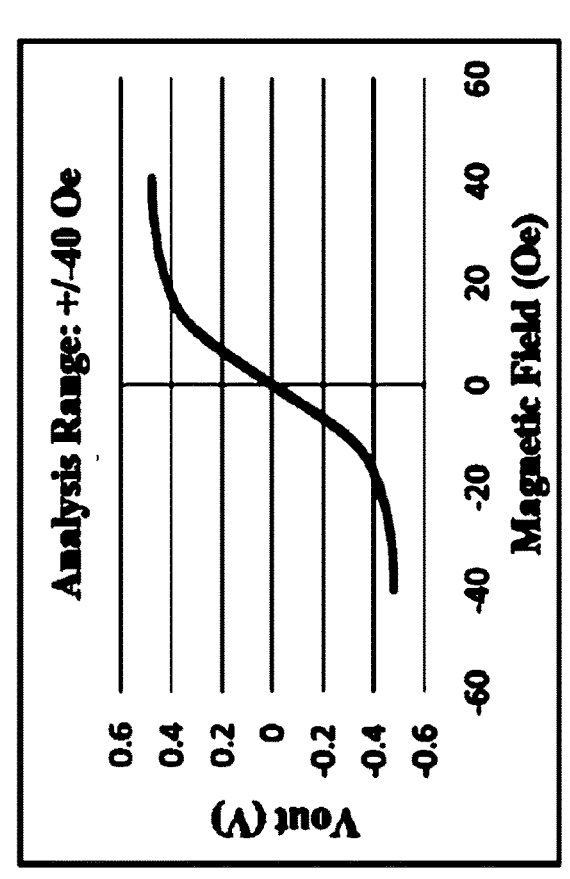
FIG. 4C
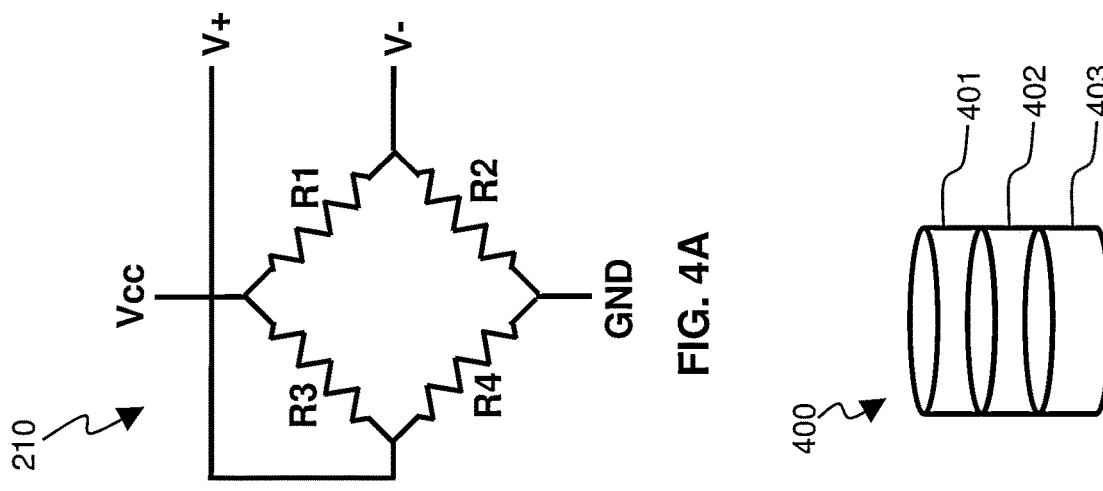
FIG. 4A
FIG. 4D $$(wk)^2 = (x-3D)^2 + y^2$$
$$(vk)^2 = (x-2D)^2 + y^2$$
$$(uk)^2 = (x-D)^2 + y^2$$
$$tk^2 = k^2 = x^2 + y^2$$

SYSTEM AND METHOD FOR DISPLAYING THE LOCATION OF A FERROMAGNETIC OBJECT IN A LIVING ORGANISM

This application is a continuation-in-part of U.S. application Ser. No. 16/947,890 filed 23 Aug. 2020, the entire contents of which are incorporated by reference herein.

FIELD OF INVENTION

The present invention relates to systems and methods for detecting and displaying unintended foreign objects inside of a human or other animal. Embodiments of the invention can assist human or veterinary surgery personnel to detect and retrieve retained ferromagnetic or ferrimagnetic foreign bodies during or after surgery. Examples of foreign bodies that could be detected and removed can include tools, surgical needles, and sponges that comprise ferromagnetic or ferrimagnetic material.

BACKGROUND

Retained foreign bodies occur in 0.03% to 0.1% of human abdominal surgical cases. (Source: US National Library of Medicine). Foreign objects can inadvertently be retained as a result of: (a) a miscount by the operating room staff; (b) a change in surgical technique from the standard protocol/steps; (c) defective surgical materials, instruments or equipment; (d) a prolonged surgical case with multiple operating room teams; (e) and/or when multiple procedures are performed synchronously or successively under the same anesthetic. When an unintended retained foreign body was present after surgery, about 30% of patients required readmission and 83% of patients required reoperation. The average cost of an unintended retained foreign body after surgery was about $95,000 in 2008, including about $15,000 in medical costs with the remainder being for legal expenses (Source: journals.sagepub.com).

The prior art for minimizing retained bodies includes optimized communication by operative team members, surgical counts, bar code scanning, radio-frequency detection and identification, and x-ray technology. Problems with manual and team methods includes miscounts reported as correct, surgeon error, and defective surgical materials or equipment.

Prior art radio-frequency based systems are typically limited to items with radiofrequency tags. Such radio-frequency approaches are not designed to identify small items such as retained needles nor do these prior art techniques easily localize tagged items.

X-ray/fluoroscopy detection has many limitations. The efficacy of x-ray is limited based on patient body habitus (x-ray penetration), surgical position (affects how x-ray can be delivered and penetrate the patient), and accessibility for radiologist reading during surgery, as well as size of retained item for an accurate reading. There is also an exposure risk to the patient and operating room team from the radiation, especially during pregnancy, etc.

Limited access and visualization of the surgical field complicates visual detection of lost, dislodged, or retained foreign bodies during minimally invasive surgery. Foreign objects or fragments can be unseen and/or lost in the surgical field. A camera and handheld or robotic instruments to manipulate the operative field are typically used in such "keyhole" procedures.

Metal detectors that rely on electrical conductivity have difficulty finding small retained objects (needles, suture fragments, staples, etc.). Such metal detectors generate an electromagnetic field, using an alternating current in a conductive coil, to produce eddy currents in conductive metal and then sense changes to the electromagnetic field created by the induced eddy currents. Small metal fragments, and small items such as surgical needles, have a small cross-sectional area, and therefore the induced eddy currents do not produce a detectable change to the electromagnetic field. It is also preferable to have a foreign object detector that does not generate electromagnetic field, which some consider unhealthy.

If a foreign body is detected, it needs to be located in three-dimensional space. Therefore, it is highly desirable to have a display that can clearly and accurately guide the operating room personnel to the location of the foreign body.

If a presumed foreign body cannot be located or localized using available detection methods, the surgical procedure must be converted from a minimally invasive approach to traditional open surgery. In the event of conversion to open conventional surgery, length of patient hospitalization, pain medication requirements, time to return to regular activity, overall patient morbidity, and cosmesis requirements all increase.

It is also desired to have better systems and methods for detecting ferromagnetic objects in situations other than surgery. One example is the need to non-invasively detect ferromagnetic objects in a human body prior to conducting magnetic resonance imaging (MRI).

For the above reasons, better tools and techniques are needed for detecting a retained foreign body. A safe, effective, and low-cost system and method for detecting items used during conventional and minimally-invasive surgery would save many lives, reduce surgical costs, and reduce legal malpractice costs.

BRIEF DESCRIPTION OF THE DRAWINGS

This disclosure is described in conjunction with the appended figures in which:

FIG. 4A is a tunneling magnetoresistance (TMR) Wheatstone bridge circuit for use in the ferromagnetic object detectors of FIG. 1A to FIG. 3;

FIG. 4B shows the voltage response of the TMR circuit of FIG. 4A to small changes in magnetic field strength;

FIG. 4C shows the voltage response of the TMR circuit of FIG. 4A to large changes in magnetic field strength that saturate the TMR sensor;

FIG. 4D shows two ferromagnetic layers separated by an insulating barrier of a magnetic tunnel junction in a TMR sensor;

Figures 1A, 1B, 1C:
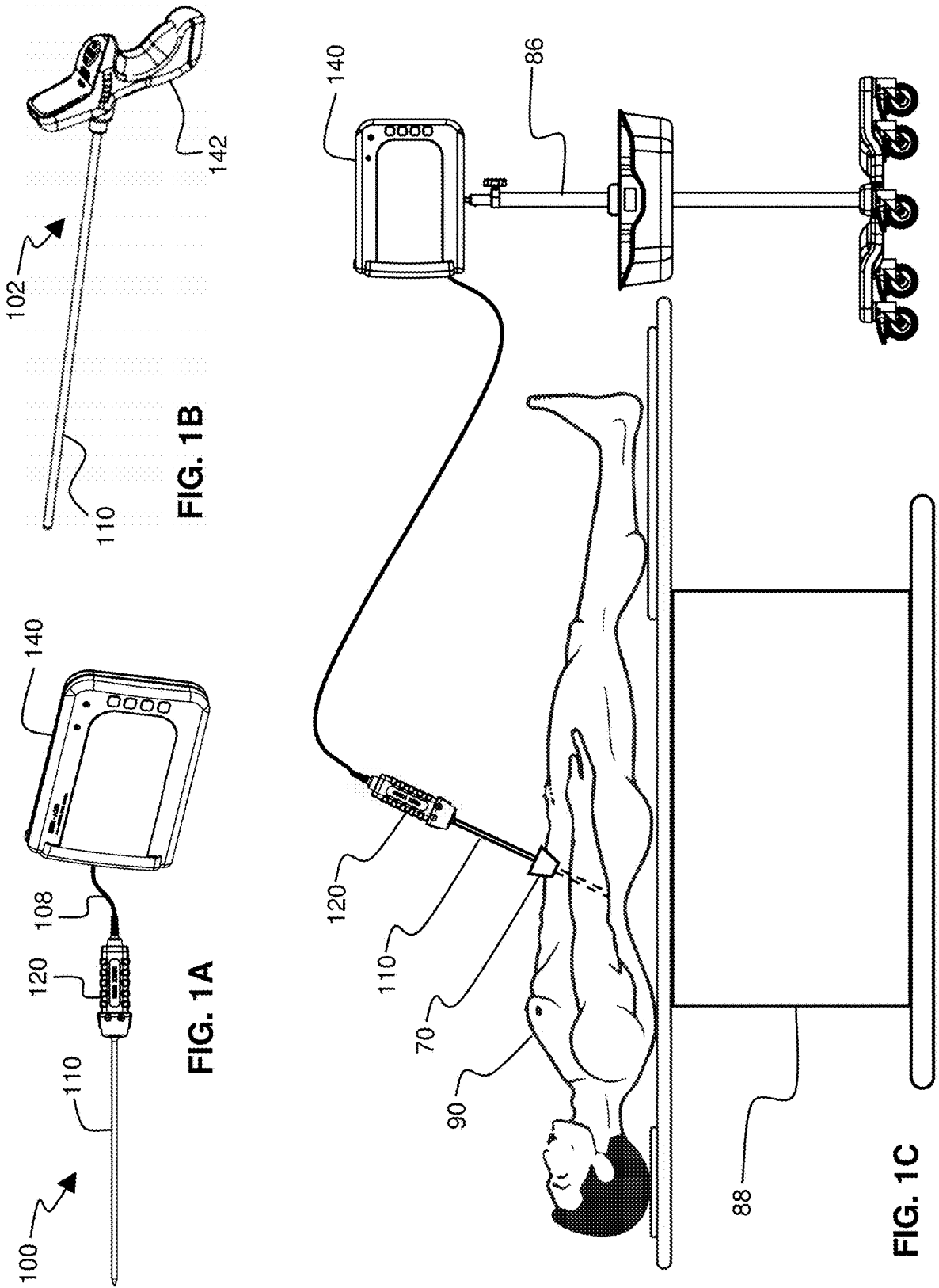
FIG. 1A shows a surgical ferromagnetic object detector.
FIG. 1B shows an alternate embodiment of a surgical ferromagnetic object detector.
FIG. 1C shows the ferromagnetic object detector of FIG. 1A used in a patient.

It should be understood that the drawings are not necessarily to scale. In certain instances, details that are not necessary for an understanding of the invention or that render other details difficult to perceive may have been omitted. It should be understood that the invention is not necessarily limited to the particular embodiments illustrated herein.

DETAILED DESCRIPTION

The ensuing description provides preferred exemplary embodiment(s) only, and is not intended to limit the scope, applicability or configuration of the disclosure. Rather, the ensuing description of the preferred exemplary embodiment(s) provides those skilled in the art with an enabling description for implementing a preferred exemplary embodiment. It should be understood that changes could be made in the function and arrangement of elements without departing from the spirit and scope as set forth in the appended claims.

Specific details are given in the following description to provide a thorough understanding of the embodiments. However, it will be understood by one of ordinary skill in the art that the embodiments may be practiced without these specific details. For example, those skilled in the art will know that different circuitry, transducers, materials, processes, configurations, and components may be substituted.

1. Definitions

In embodiments of the invention and claims, magnetism is physical phenomenon that works similarly to the attraction for pure iron produce by lodestone. A magnetic source is any material or process (e.g. electromagnetism) that creates magnetism. A ferromagnetic material is a substance that exhibits magnetism because (a) it behaves like lodestone in being attracted to pure iron (i.e. it is a permanent magnet) or (b) it behaves like pure iron in being attracted to a permanent magnet. Examples of ferromagnetic materials include, but are not limited to, cobalt, iron, various ferric oxides, nickel, and rare earth magnets.

In embodiments of the invention and claims, a magnetic field is a region around a magnetic source in which a magnetism acts. Magnetic fields can occupy a large region (e.g. earth's magnetic field) or they can be detectable in only a small region, such as the electro-magnetic field surrounding a wire carrying an electric current. Magnetic flux is the normal component of a magnetic field passing through a surface. Magnetic flux lines show the direction of a magnetic field.

In embodiments of the invention and claims, a ferrimagnetic material is a substance that has groups of atoms with unequal opposing magnetic moments, resulting in a detectable magnetic field. Examples of ferrimagnetic materials include magnetite ($Fe_3O_4$), yttrium iron garnet (YIG), cubic ferrites composed of iron oxides with other elements such as aluminum, manganese, and zinc, and hexagonal ferrites such as $PbFe_{12}O_{19}$ and $BaFe_{12}O_{19}$ and pyrrhotite ($Fe_{1-x}S$). In embodiments of the invention and claims, ferrimagnetic materials are defined as a type of ferromagnetic material.

The terms ferromagnetic and ferrous should not be confused. Ferrous materials contain iron. There are ferromagnetic materials (such as cobalt, nickel, and rare earth magnets) that are not ferrous (do not contain iron). There are ferrous (iron-containing) materials (such as austenitic stainless steels) that are not ferromagnetic. Not all stainless steels are austenitic. Martensitic stainless steels are ferromagnetic.

Metal detectors work on a different principle than the ferromagnetic detectors described herein. Metal detectors rely on electrical conductivity of a metal. The ferromagnetic object detectors described herein:

(a) detect ferromagnetic materials;
  (b) do not detect metals if they are not ferromagnetic;
  (c) do not detect ferrous materials if they are not ferromagnetic; and
  (d) detect non-metals and non-ferrous metals if they are ferromagnetic.

The following table gives examples of ferrous, ferromagnetic, and metal objects to illustrate differences in what is detected by a metal detector and a ferromagnetic object detector based on the above description of what each detector can sense:

| Material | Ferromagnetic | Ferrous | Metal |
|---|---|---|---|
| Iron | Yes | Yes | Yes |
| 316 stainless steel | No | Yes | Yes |
| 410 stainless steel | Yes | Yes | Yes |
| Nickel | Yes | No | Yes |
| Titanium | No | No | Yes |
| Aluminum | No | No | Yes |
| Rare earth magnet | Yes | No | No |
| Polyethylene plastic | No | No | No |

In embodiments of the present invention and claims, passive ferromagnetic object detection means sensing a ferromagnetic object in an ambient magnetic field. Passive ferromagnetic object detection systems do not rely on actively creating a local magnetic field and/or local electromagnetic field to detect ferromagnetic objects.

In embodiments of the invention and claims, a magnetic sensor is a transducer that measures strength, orientation, and/or a change in strength/orientation of a magnetic field. The terms magnetic sensor and magnetometer are interchangeable in describing embodiments of the invention and claims. Magnetic sensors can operate using a variety of principles and can have a variety of outputs such as voltages, currents, and/or resistances. Examples of magnetic sensors include, but are not limited to, magnetic compasses, superconducting quantum interface devices (SQUIDs), antennas, inductive pickup coils, and fluxgate magnetometers.

In embodiments of the invention and claims, a magnetoresistance sensor is a magnetic sensor that exhibits electrical resistance in response to a magnetic field. Examples of magnetoresistance sensors include tunneling magnetoresistance (TMR) sensors, Hall effect sensors, anisotropic magnetoresistance (AMR) sensors, giant magnetoresistance (GMR) sensors, and/or magnetodiodes.

In embodiments of the invention and claims, a background electrical signal is defined as unwanted information that can accompany a transmitted electrical signal as a result of the environment in which an electrical signal source (such as a sensor) operates.

In embodiments of the invention and claims, electrical noise is defined as irregular electrical fluctuations that accompany a transmitted electrical signal, but are not part of it, and tend to obscure it. In embodiments of the invention and claims, background subtraction is the removal of a background signal from a signal to more effectively process information of interest. In embodiments of the invention and claims, noise cancellation is defined as the removal of noise from a signal.

2. Overview of One Embodiment of the System and Method

In one embodiment, the present invention comprises a device or method for locating a ferromagnetic object in a living or non-living human or animal (i.e. organism) configured to use spatial differences in a magnetic and/or electromagnetic field at two locations to detect a ferromagnetic object, wherein the first location is internal to a body cavity and the second location is external to the body cavity. The system or method:

(a) Could comprises one or more magnetic sensors at the first location and one or more magnetic sensors at the second location wherein the magnetic sensors used by the device could be magnetoresistance sensors and more specifically, the magnetoresistance sensors could be tunneling magnetoresistance (TMR) sensors;

(b) Could be configured to use background subtraction and/or noise cancellation to remove a signal responsive to sensor at the second (external) location from a signal responsive to a sensor at the first (internal) location;

(c) Could be configured for conventional open surgery and/or for minimally invasive surgical procedures using minimally-invasive ports;

(d) Could provide a detection method that is absent of radioactivity and not dependent on a tracer detection system;

(e) Does not generate a magnetic field, but instead detects one or more ferromagnetic objects based on a change in the earth's ambient magnetic field caused by a ferromagnetic object;

(f) Could be configured to detect ferromagnetic objects in and out of the surgical field of view and/or in or out of a human or animal body cavity, both living and non-living;

(g) Could be configured as a wired or wireless handheld device;

(h) Could be configured to communicate with a remote device for programming and/or recording information;

(i) Could be configured to record details of scan history including but not limited to time, date and location;

(j) Could be configured to generate audible sounds, visual cues, and/or tactile information that vary based on proximity and/or direction to an object;

(k) Could be powered by a battery, a wireless power source, and/or a wired power source;

(l) Could comprise an articulating tip;

(m) Could have adjustable sensitivity of detection; and/or (n) Could comprise a display, or interface with a display, that shows the location of any detected ferromagnetic object relative to the location of a probe tip in three dimensions.

3. Functional Description of Embodiments of the Ferromagnetic Object Detector

Referring now to illustrations of the embodiments, FIG. 1A shows a surgical ferromagnetic object detector 100. This ferromagnetic object detector 100, and other embodiments described herein, can also detect ferrimagnetic objects. The ferromagnetic object detector 100 comprises a probe shaft 110, a probe handle 120 for holding and moving the probe, and a system controller 140. In the embodiment shown in FIG. 1A, the controller 140 is connected to the probe handle 120 with a cable 108. FIG. 1B shows an alternate embodiment of a surgical ferromagnetic object detector 102 which has a combined probe handle and system controller 142. The probe shaft 110 for the alternate embodiment in FIG. 1B can be functionally identical to the probe shaft 110 for the detector in FIG. 1A. Referring to FIG. 1A and FIG. 1B, the probe shaft 110 can be 35-50 cm long depending upon the application. The shaft 110 could be cylindrical. It could be 1-15 mm in diameter. It could be comprised of a plastic or a surgical grade non-ferromagnetic metal covering depending upon whether the shaft 110 is disposable or reusable. The shaft could comprise an internal counter that renders it expired after a pre-defined number of uses. The shaft 110 could comprise an articulating and/or telescoping tip located at its distal end. The shaft 110 could comprise a central flushing port for sterile processing.

Alternate embodiments of the ferromagnetic object detector can include:

(a) A system such as that shown at 100 in FIG. 1A or 102 in FIG. 1B in which all components are sterilizable and reusable;

(b) A system such as that shown at 100 in FIG. 1A or 102 in FIG. 1B in which the probe 110 is user removable and disposable;

(c) A system such as that shown at 102 in FIG. 1B in which the entire unit is factory-sterilized, and useable for a limited number of times before it is disposed, in order reduce the cost and complexity of re-sterilizing combined probe handle and system controller; and/or (d) Any combination of reusable and disposable components capable of being understood by anyone skilled in the art.

If one or more components of the ferromagnetic object detector can be used for one time, or for a limited number of times, these components could comprise circuitry that counts the number of times that component has been used and disables that component exceeds its life or calibration period. The system could also comprise a pathogen detector or temperature sensor that is configured to identify if that component has not been properly sterilized.

FIG. 1C shows the surgical ferromagnetic object detector 100 of FIG. 1A when used with a human patient 90 on a surgical operating table 88. In FIG. 1C, the probe shaft 110 is configured to be partially inserted into a body cavity of the patient 90 through a surgical insertion port 70. The surgical insertion port 70 is a medical access device. The specific surgical insertion port 70 shown in FIG. 1C comprises a trocar configured for placement through an abdomen during laparoscopic surgery. This same configuration could be used for other types of minimally-invasive surgery, such as thoracoscopic surgery. This trocar comprises a cannula, in the form of a hollow tube through which at least part of the probe shaft 110 is inserted into the abdomen of the patient 90. In addition to the probe shaft 110, probe handle 120, and system controller, the system in FIG. 1C also comprises a surgical trolley 86 for holding the system controller 140.

Figure 2:
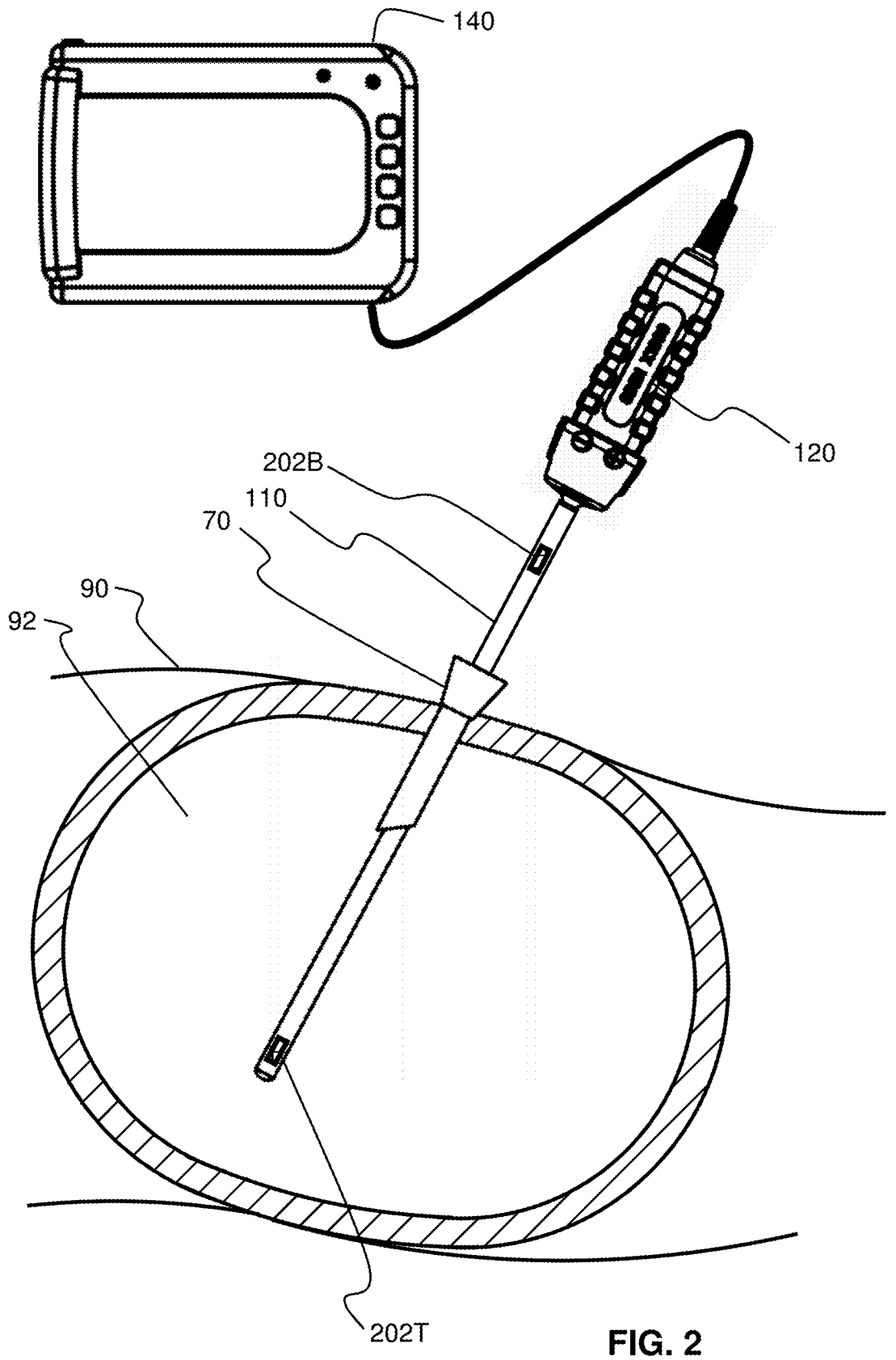
FIG. 2 shows the detector of FIG. 1A with the probe tip inserted into a body cavity.

FIG. 2 shows a more detailed view of the surgical ferromagnetic object detector of FIG. 1A, when partially inserted through the insertion port 70 into a body cavity 92 of a human patient. The human body cavity 92 could be any internal part of a human (or animal) patient 90. Thus, FIG. 2 is similar to FIG. 1C, but shows more internal details of the body cavity 92, probe shaft 110, and surgical insertion port 70. The probe shaft 110 comprises a probe tip magnetic sensor 202T that is located on the distal end of the probe shaft 110. The probe tip sensor 202T is configured for insertion into the body cavity 92. The probe shaft 110 comprises a probe base magnetic sensor 202B that is located on the proximal end of the probe shaft 110 near the probe handle 120. The probe base magnetic sensor 202B is configured for staying outside of the body cavity 92. Information received by the probe tip magnetic sensor 202T and probe base magnetic sensor 202B can be processed in the probe handle 120 and system controller 140, as will be further described later in this document. In the embodiment shown in FIG. 2 the probe tip magnetic sensor 202T and probe base magnetic sensor 202B comprise tunneling magnetoresistance (TMR) sensors, described in greater detail later herein.

Figure 3:
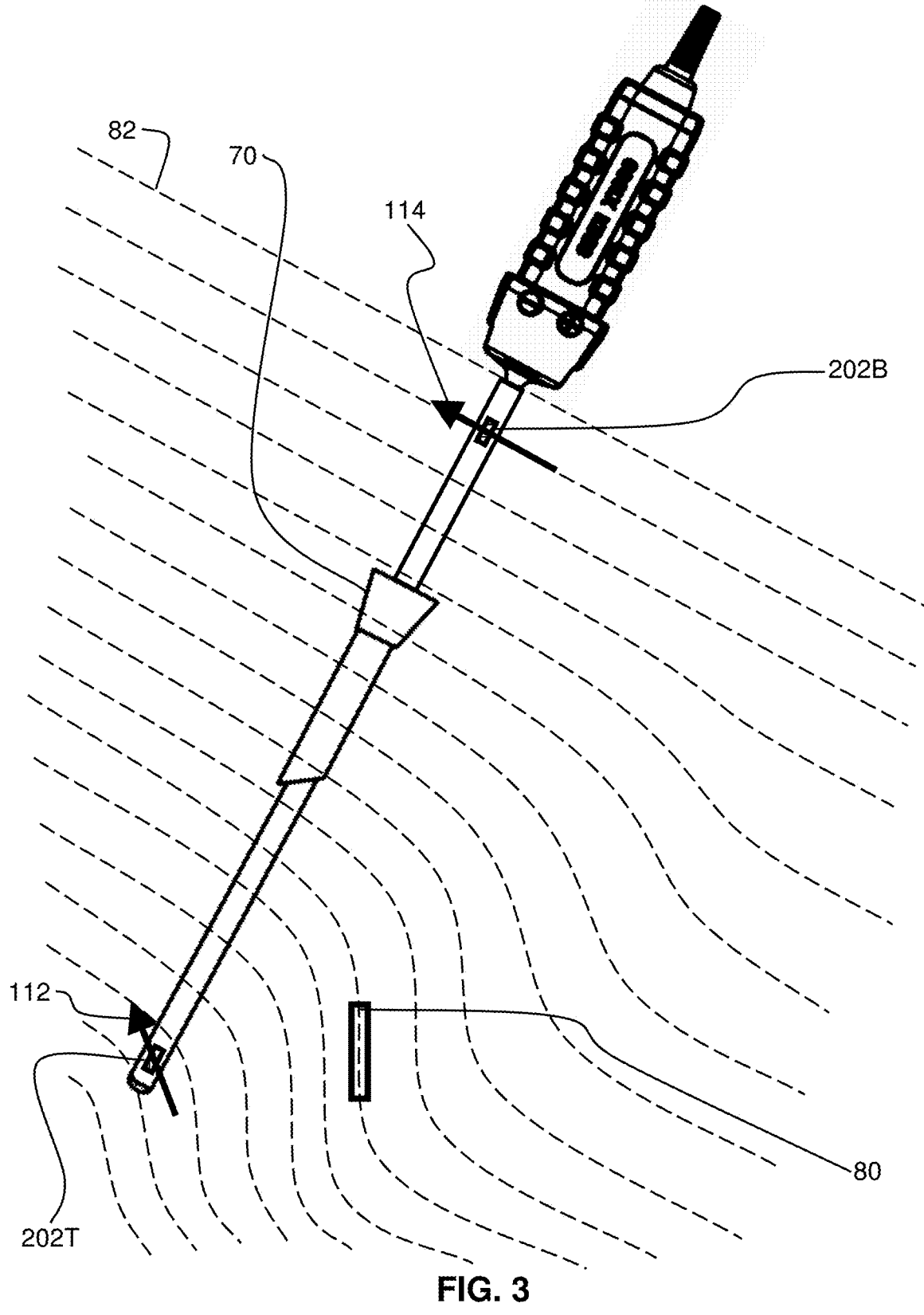
FIG. 3 shows a two-dimensional view of the influence of a ferromagnetic object on (a) magnetic flux lines and (b) a pair of magnetic sensors in the probe of FIG. 1A.

FIG. 3 shows the influence of a ferromagnetic object 80 on a magnetic field vector 112 at a probe base magnetic sensor 202B and a magnetic field vector 114 at a probe tip magnetic sensor 202T that has been inserted through a minimally invasive port 70. The dotted lines 82 provide a 2-dimensional visualization of the magnetic flux lines 82 in the region surrounding the ferromagnetic object 80. It can be seen in FIG. 3 that this ferromagnetic object 80 distorts the magnetic flux 82 in its proximity. Because the ferromagnetic object 80 is located closer to the distal end of the probe shaft, the magnetic field 112 measured by the probe tip magnetic sensor 202T is affected more than the magnetic field 114 measured by the probe base magnetic sensor 202B. By subtracting the magnetic probe base sensor signal 114 from the magnetic probe tip sensor signal 112, the system can be configured to detect ferromagnetic objects that affect the tip sensor 202T differently than the base sensor 202B.

4. Magnetoresistance and Tunneling Magnetoresistance (TMR) Technology

Magnetic transducers (also referred to as magnetic sensors or magnetometers) can be used to sense magnetic field strength and to measure current, position, motion, direction, and other physical parameters. Embodiments of the inventions described herein can use highly sensitive low-cost magnetic sensors at the probe base 202T and the probe tip 202B in FIG. 3. Magnetoresistance sensors are one type of magnetic transducer that can be used in embodiments of the invention. Examples of magnetoresistance sensors include Hall effect sensors, magneto-diodes, anisotropic magnetoresistance (AMR) sensors, giant magnetoresistance (GMR) sensors, and tunneling magnetoresistance (TMR) sensors. The table below compares some of these sensor technologies:

|  | Hall | AMR | GMR | TMR |
|---|---|---|---|---|
| Sensitivity | Low | Medium | High | Highest |
| Temperature stability | Medium | Medium | Medium | High |
| Linear operating range | Poor | Poor | Poor | Good |
| Power consumption | High | Medium | Low | Low |
| Additional device requirements | Flux concentrator | Set/reset coil | None | None |
| Cost | High | Medium | Medium | Low |

The above table shows that TMR (tunneling magnetoresistance) sensors have the highest sensitivity and low cost. TMR sensors can be used with background subtraction and noise cancellation to optimally detect a foreign ferromagnetic body in an organism without needing to generate a magnetic or electromagnetic field—i.e. the resulting device or system passively detects changes in an ambient magnetic field caused by ferromagnetic objects.

Magnetoresistance of a magnetic tunnel junction (MTJ), also known as tunneling magnetoresistance (TMR), is a result of the spin-dependent tunneling effect. As shown in FIG. 4D, the typical structure of an MTJ 400 is two ferromagnetic (FM) layers, 401 and 403, separated by a thin insulating (I) barrier 402, in a FM/I/FM configuration, sometimes referred to as a "sandwich structure." In sensor applications, one ferromagnetic layer 401 (the pinned layer) is usually designed with magnetization that does not move in response to an applied magnetic field. The other ferromagnetic layer 403 (the free layer) is designed such that the magnetization moves easily in response to the applied magnetic field. The relative magnetization orientation of of the pinned 401 and free 403 layers is representative of the strength and direction of the applied magnetic field. Because the tunneling probability for electrons to cross the insulating barrier 402 is dependent upon the relative orientation of the free 403 and pinned 401 layer magnetizations, the resistance of an MTJ 400 indicates the applied magnetic field in a specific direction.

To get around the issue that electrical resistance is difficult to measure directly, a TMR sensor, or other type of magnetoresistance device can be configured into a tunneling magnetoresistance Wheatstone bridge circuit as shown at 210 in FIG. 4A. When a constant voltage is applied between Vcc and GND, the voltage between V+ and V− will vary depending upon the resistances R1, R2, R3, and R4 based on the following equation:

$$V_{out}=(V+)-(V-)=(V_{cc})[(R4/(R3+R4))-(R2/R1+R2))]$$

In a typical TMR Wheatstone bridge circuit 210, R1, R2, R3, and R4 are magnetic tunneling junctions (MTJs), with R1 and R4 having the pinned and free layers reversed from R2 and R3 so that the resistance will increase in R1 and R4 when the resistance in R2 and R3 decreases, and vice versa. Such a Wheatstone bridge circuit 210 with four magnetic tunneling junctions (MTJs) can be fabricated on a semiconductor wafer and packaged as a low-cost sensor. FIG. 4B and FIG. 4C show the relationship between Vout and magnetic field strength in Oersteds (Oe) for the TMR Wheatstone bridge circuit 210 of FIG. 4A that uses 4 magnetic tunneling junctions (MTJs) and has an applied voltage (between Vcc and ground) of 1 volt. FIG. 4B shows that a typical TMR Wheatstone bridge circuit, 210 in FIG. 4A, exhibits a linear relationship between magnetic field strength (intensity) in the range of +/−5 Oersteds with a slope of about 30 millivolts/Volt/Oersted. FIG. 4C shows that this typical TMR Wheatstone bridge circuit, 210 of FIG. 4A, exhibits a non-linear response and saturates for larger magnetic field strengths. The earth's magnetic field has an intensity on the order of 0.5 Oersteds, which is the same as 0.5 Gauss or 50 microTesla. More specifically, the intensity of the earth's magnetic field ranges from 0.3 gauss far away from the earth's magnetic poles to 0.6 gauss near the earth's magnetic poles. This means, that the typical TMR Wheatstone bridge circuit will operate in the linear region (shown in FIG. 4B) when measuring ambient magnetic fields that are of the same order of magnitude as the earth's magnetic field (i.e. distortions of the earth's magnetic field caused by nearby ferromagnetic objects). If Vcc is 1 volt and the distortion of the earth's magnetic field is half of the magnetic field, or a change in strength of 0.25 Oersteds at a particular location, a typical TMR Wheatstone bridge circuit with a linear response of 30 mV/V/Oe would exhibit an output voltage change of 15 mV (0.25×30×2). This 15 mV peak-to-peak is a reasonable signal to be processed by an instrumentation amplifier or directly by an analog to digital converter.

If two TMR Wheatstone bridge circuits with identical output characteristics are placed perpendicular to each other and powered by the same excitation voltage (Vcc), one can build the equivalent of an electronic compass that will identify the angle between the current orientation of the electronic compass in a plane parallel to the earth's surface and magnetic north using the following equation:

$$\text{Angle} = \text{Arctangent}(Vx,\ Vy)$$

Where:
Angle is the angle between electronic compass and magnetic north
Arctangent is an inverse tangent function that returns an angle between −180 degrees and +180 degrees as a function of positive or negative values of X and Y.
Vx is the output voltage (difference between V+ and V−) for the Wheatstone bridge having magnetic tunneling junctions oriented in the X-axis.
Vy is the output voltage (difference between V+ and V−) for the Wheatstone bridge having magnetic tunneling junctions oriented in the Y-axis.

Similarly, if three TMR Wheatstone bridge circuits are placed orthogonally, one can measure both the direction and the strength of a magnetic field at a particular location as a 3-dimensional vector. One such 3-axis TMR sensor unit is shown at 200 in FIG. 5. Referring to the details of FIG. 5, the 3-axis TMR sensor unit 200 comprises three tunneling magnetoresistance Wheatstone bridge circuits, for the X-direction, Y-direction, and Z-direction, shown at 210X, 210Y, and 210Z, respectively. The differential voltage output of each TMR Wheatstone bridge circuit (210X, 210Y, and 210Z) is fed into an analog electrical amplifier, shown at 212, and this amplified analog output is converted to a digital binary signal using an analog to digital converter, shown at 214, to produce digital signals responsive to the ambient magnetic field, shown at 216X for the X-direction, 216Y for the Y-direction, and 216Z for the Z-direction. The analog electrical amplifiers, shown at 212 are typically semiconductor-based instrumentation amplifiers the use and implementation of which are understood by those skilled in the art.

Figure 5:
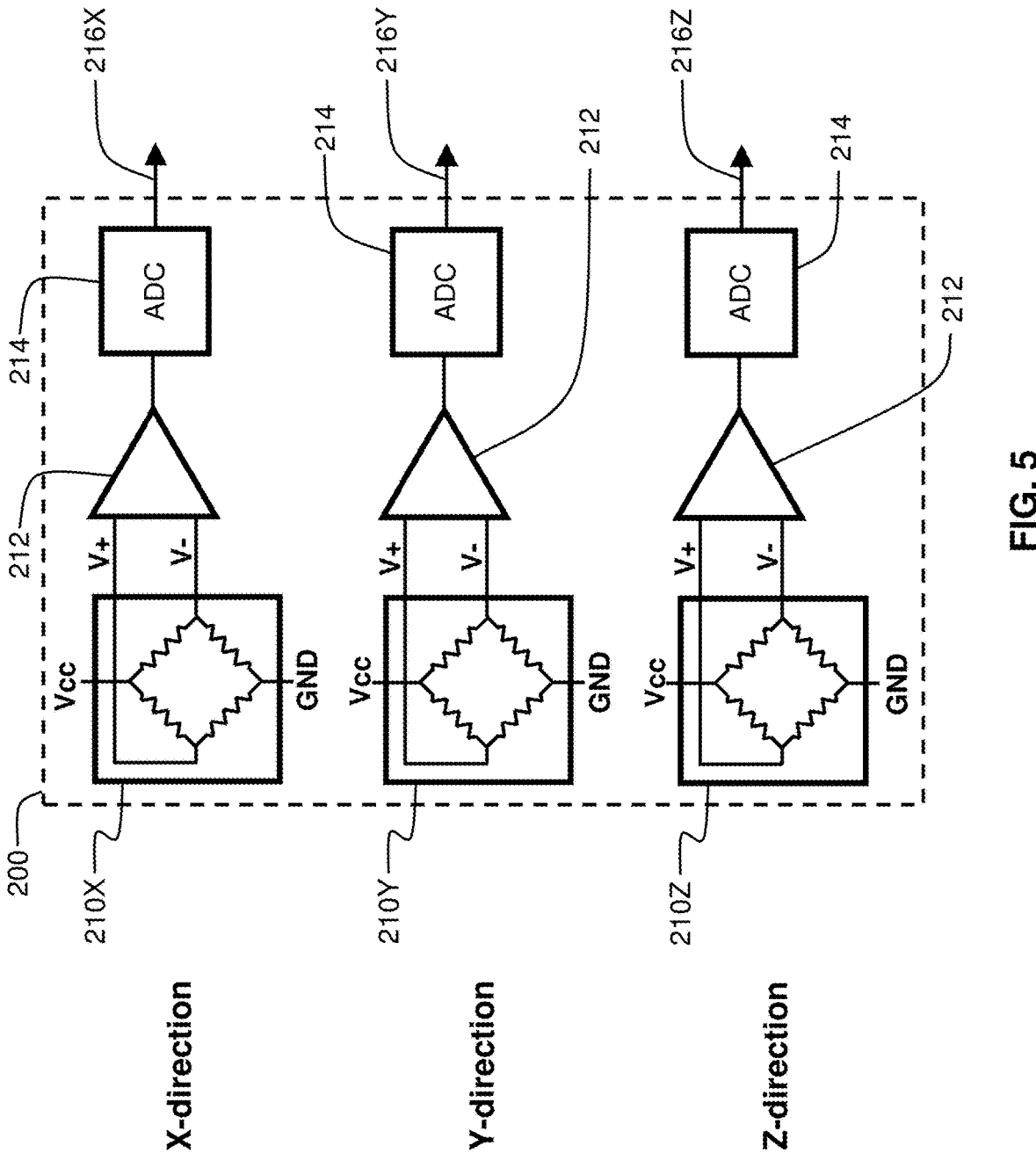
FIG. 5 shows a 3-axis sensor unit that comprises three TMR circuits of FIG. 4A.
Figure 6:
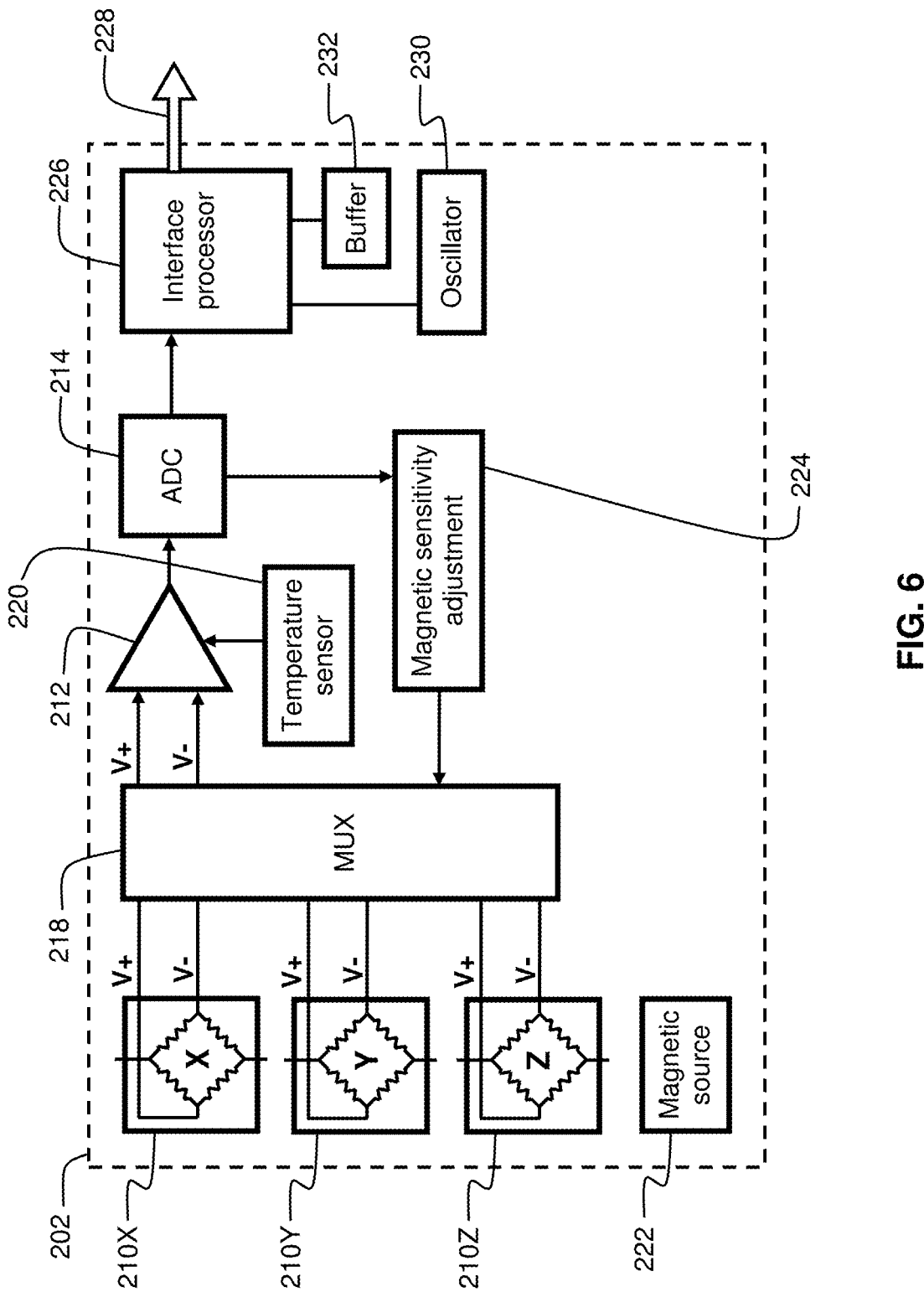
FIG. 6 shows a-3-axis TMR sensor module similar to the sensor unit of FIG. 5.

TMR sensors, such as those shown FIG. 4A and at 210X, 210Y and 210Z in FIG. 5 are influenced by temperature. Therefore, it is beneficial to provide temperature compensation to the circuit shown at 200 in FIG. 5. When packaging the three TMR bridge circuits into a single sensor module, it is also beneficial to provide other reference and compensation circuits, and to provide an interface to a standard digital bus architecture. FIG. 6 illustrates a compensated 3-axis TMR sensor module at 202. Referring to FIG. 6, the 3-axis TMR sensor module 202 comprises the three TMR Wheatstone bridge circuits 210X, 210Y, and 210Z The low-level analog outputs from these TMR Wheatstone bridge circuits are fed into an analog signal multiplexer, shown a 218 and then selectively fed into the analog electrical amplifier 212, which outputs to the analog to digital converter 214. Temperature compensation can be built into the sensor module 202 by including a temperature sensor 220 that generates a voltage as a function of temperature. In the embodiment shown, the analog amplifier 212 is responsive to the temperature sensor 220 to compensate for temperature changes in the output signals from the TMR Wheatstone bridge circuits (210X, 210Y, and 210Z) that are provided by the multiplexer 218. An on-board magnetic source 222 can be used to generate a reference magnetic field to calibrate the TMR Wheatstone bridge circuits (210X, 210Y, and 210Z) and magnetic sensitivity can be adjusted using a magnetic sensitivity adjustment circuit 224 that uses a reference voltage.

Further referring to FIG. 6, the output from the analog to digital converter 214 can be transmitted to other electronic devices over an electronic interface 228 using an interface processor 226. The interface processor 226 could generate a signal using a protocol such as I$^2$C, a 4-wire serial protocol (commonly written as I2C), or any other protocol capable of being understood by anyone skilled in the art. The interface processer 226 could be responsive to an oscillator 230 and the module could comprise a data buffer 232 to store digitized magnetic field strength readings until they can be transmitted via the electronic interface 228. The electronic interface 228 can comprise the digital signals shown at 216X, 216Y, and 216Z in FIG. 5.

Summarizing the information discussed with reference to FIG. 4A, FIG. 4B, and FIG. 4C, a TMR sensor when used in a Wheatstone bridge circuit with an applied constant voltage will generate a voltage signal in response to the applied magnetic field. This voltage signal is typically in the range of millivolts. Summarizing the information presented in FIG. 5 and FIG. 6, this voltage signal can be amplified, it can be digitized, it can be measured in three orthogonal axes, and it can be improved through compensation for temperature, calibration with a reference magnetic field, and adjusted for sensitivity. The sensor unit shown at 200 in FIG. 5 and the sensor module shown at 202 in FIG. 6 are configured to be responsive to changes in magnetic field orientation and magnetic field strength in three axes.

Referring to the magnetic field vector if the probe tip, shown at 112 in FIG. 3, and the magnetic field vector at the probe base, shown at 114 in FIG. 4, if two 3-TMR-sensor units, shown at 200 in FIG. 5, are spatially separated, it is possible to measure the spatial variation of an ambient magnetic field between the location of a first 3-TMR-sensor unit and a second 3-TMR-sensor unit. Thus, TMR (or some other magnetic sensor technology) can be used in embodiments of the invention to detect a spatial variation in an ambient magnetic field caused by one or more ferromagnetic objects that differentially influence two spatially-separated 3-axis TMR sensor units.

Figure 7:
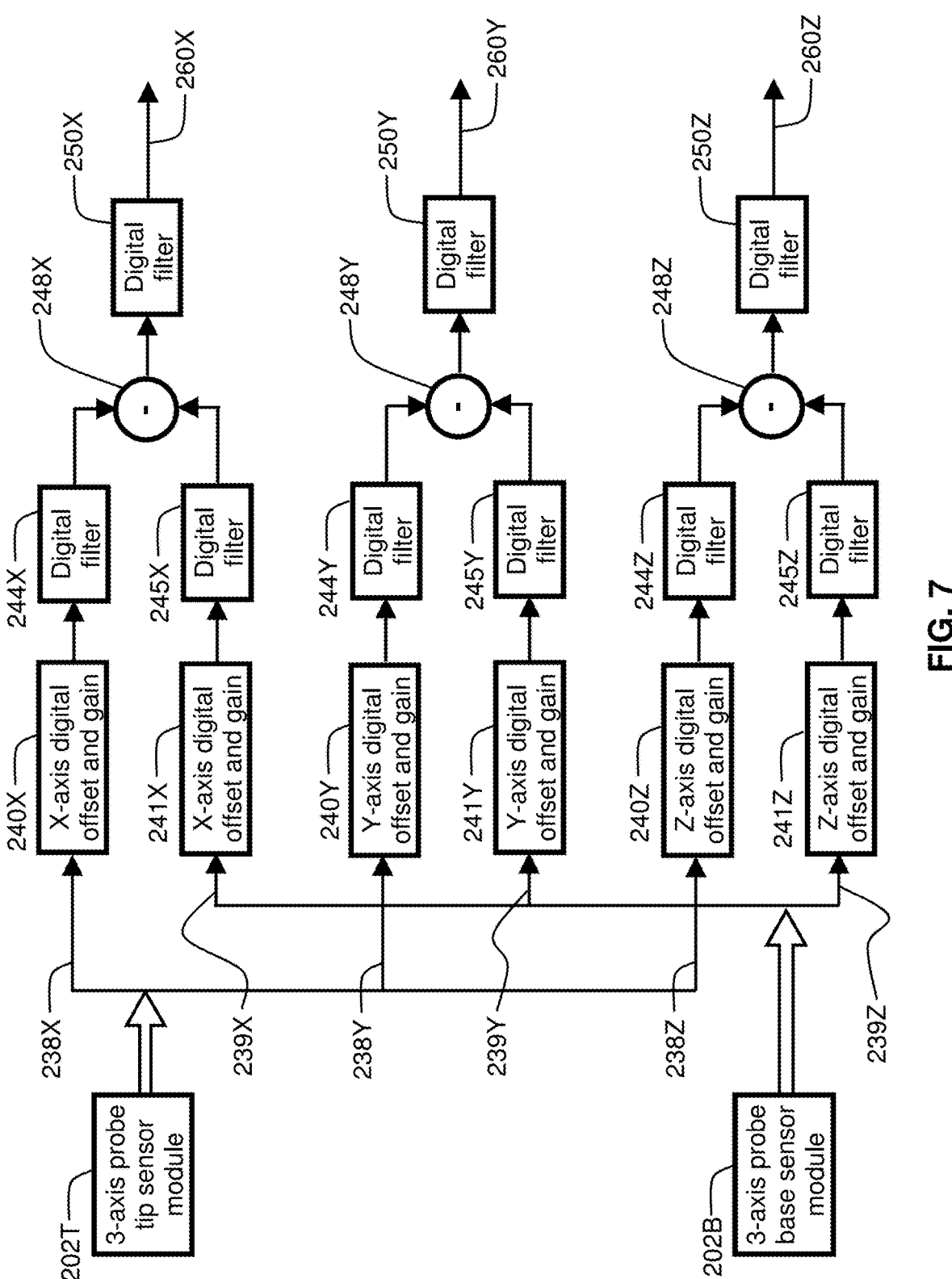
FIG. 7 shows two integrated 3-axis TMR sensor modules configured for use as part of the ferromagnetic object detectors FIG. 1A to FIG. 3.

This differential measurement of an ambient magnetic field can be more accurate with compensation for temperature and other factors by using three-axis sensor modules such as those shown at 202 in FIG. 6 are used. Referring to FIG. 3, FIG. 6, and FIG. 7, two of the three-axis sensor modules shown at 202 in FIG. 6 can be used in the device of FIG. 3. The probe tip sensor module has been labeled 202T in FIG. 3, and the probe base sensor module has been labeled 202B in FIG. 3 to distinguish them from each other. Each of these two sensor modules, 202B and 202T, is responsive to the projected magnetic field in the region where it is located, as shown at 112 and 114 in FIG. 3. This projected magnetic field can comprise (a) the earth's magnetic field, (b) electromagnetic fields produced or altered by electronic equipment in the vicinity, and (c) magnetic fields generated or altered by nearly objects. Embodiments of the invention(s) herein are configured to be responsive to magnetic fields generated or altered by nearby ferromagnetic objects. Sensor modules 202B and 202T in FIG. 3 could comprise the sensor configuration shown at 200 in FIG. 5, the sensor configuration shown at 202 in FIG. 6, or any variation on this type of sensor using any magneto-resistance detection system or method capable of being understood by anyone skilled in the art.

Referring now specifically to FIG. 7, the 3-axis probe tip sensor module, previously shown in FIG. 3, is shown at 202T and the probe base sensor module, previously shown in FIG. 3, is shown at 202B. These modules, 202T and 202B, can be similar to the sensor modules shown at 202 in FIG. 6 or the sensor unit shown at 200 in FIG. 5. The output from these sensor modules, 202T and 202B, are digital signals that are responsive to the X-axis, Y-axis, and Z-axis magnetic fields in the regions of the two sensor modules, 202T and 202B. In order to use these digital signals, shown at 238X, 238Y, 238Z, 239X, 239Y, and 239Z in the embodiments described herein, the two sensors must be calibrated to determine offsets and gains, as will be described with reference to FIG. 9. This calibration process provides digital offsets and digital gain values to be applied to the output signals from the sensor modules, including:

The X-axis digital offset and digital gain for the tip sensor module, shown at 240X;

The Y-axis digital offset and digital gain for the tip sensor module, shown at 240Y;

The Z-axis digital offset and digital gain for the tip sensor module, shown at 240Z;

The X-axis digital offset and digital gain for the base sensor module, shown at 241X;

The Y-axis digital offset and digital gain for the base sensor module, shown at 241Y; and The Z-axis digital offset and digital gain for the base sensor module, shown at 241Z.

Adjusting the offset and gain of the outputs from the two 3-axis sensor modules creates a set of six normalized digital magnetic field strength signals, which can be passed through a first digital filter, as shown at 244X, 244Y, 244Z, 245X, 245Y, and 245Z in FIG. 7. Then the differences in these filtered digital signals can be determined as shown at 248X, 248Y, and 248Z, before these difference outputs are put through a second set of digital filters, as shown at 250X, 250Y, and 250Z. The result is the differential magnetic field strength signals in the X, Y, and Z direction as shown at 260X, 260Y, and 260Z.

Figure 8:
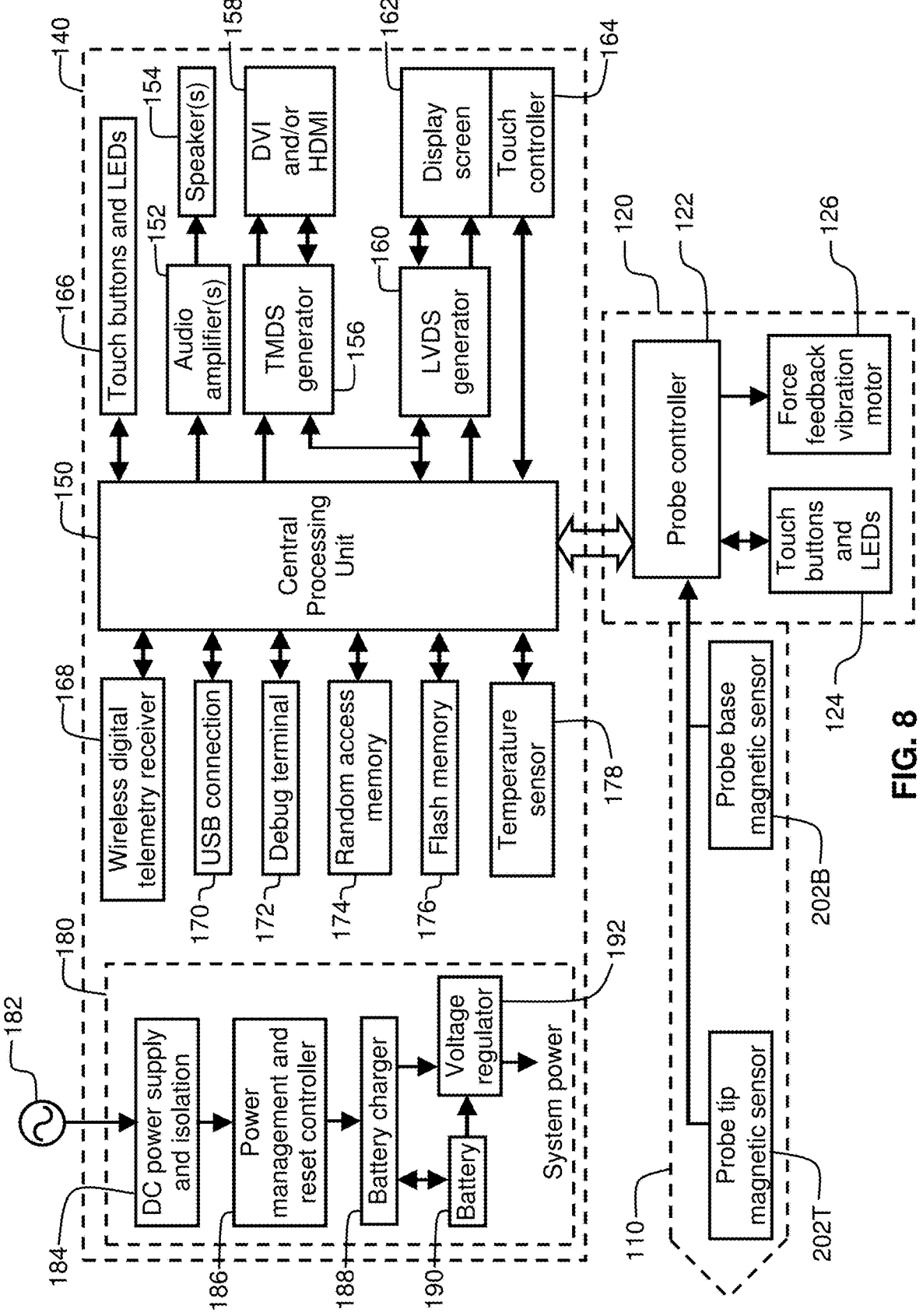
FIG. 8 is a block diagram of the ferromagnetic object detectors of FIG. 1A to FIG. 3.

5. Circuit and System Using TMR Technology in a Ferromagnetic Object Detector FIG. 8 show a block diagram of the surgical ferromagnetic object detector shown at 100 in FIG. 1A and/or the alternate ferromagnetic object detector shown at 102 in FIG. 1B using the probe base sensor module 202B and probe tip sensor module 202T shown in FIG. 3 and FIG. 7. Referring to FIG. 8, the probe tip magnetic sensor module 202T and probe base magnetic sensor module 202B, located in the probe shaft 110, communicate magnetic field information to a probe controller 122, located in the probe handle 120. The probe handle 120 can comprise touch buttons and LEDs 124, that allow the user to interact with the probe controller 122. The probe handle 120 can further comprise a force feedback vibration motor 126 that provides tactile information to the user in response to the probe controller 122, such as whether a ferromagnetic object has been detected. This tactile feedback can comprise a vibration when a foreign ferromagnetic object is detected, it can also be used to provide haptic alerts or alarms.

Further referring to FIG. 8, the probe controller 122 communicates with a system controller central processing unit 150 in the system controller 140. The controller processor (i.e., central processing unit) 150 can also communicate with other elements located in the system controller 140, such as:

(a) One or more audio amplifiers 152, which can drive one or more speakers 154, which could be used for audio alerts or alarms, and/or audio signals that vary in frequency and/or intensity in response to the detection of a ferromagnetic object and its proximity when the ferromagnetic object is detected;

(b) A transmission minimized digital signal (TMDS) generator 156 that connects to a digital visual interface (DVI) and/or high-definition multimedia interface (HDMI) 158;

(c) A low voltage differential signaling (LVDS) generator 160 that connects to a display screen 162 (typically a liquid crystal display) on the system controller 140;

(d) A touch controller 164 that works with the system controller display screen 162 to allow tactile inputs to be made to the system controller;

(e) Various system controller touch buttons and/or light emitting diodes (LEDs) 166 at allow the user to interact with the system controller central processing unit 150;

(f) A wireless digital telemetry receiver 168, such as the Xhibit (TRADE) Telemetry Receiver (XTR) made my Spacelabs Healthcare, that is configured for communicating wirelessly with other devices in a surgery suite;

(g) A universal serial bus (USB) connection 170;

(h) A debug terminal connection 172;

(i) Random access memory 174;

(j) Flash memory 176; and/or (k) A temperature sensor 178.

The wireless telemetry receiver 168 in FIG. 8 can be used to connect the system controller 140 to a variety of external devices. For example, this receiver 168 could be used to pair the system controller to an external display screen, an external input device such as a keyboard or mouse, or an external output device such as a printer. The system controller 140 could be configured to store case history data based on reference numbers for each case. This information could be transmitted via the wireless telemetry receiver 168 to a central information management system. The wireless telemetry receiver 168 could be used to connect to the manufacturer for software updates and remote device diagnostics and troubleshooting.

The system in FIG. 8 also comprises an electrical power storage and/or conversion module 180. The electrical power storage/conversion module 180 could be part of the system controller 140 or it could be external. The electrical power/conversion module 180 could be configured to receive electrical power from an external alternating current (AC) source 182. Alternating current (AC) could be converted to a direct current (DC) at a fixed voltage using a DC power supply and isolation unit 184. The direct current (DC) power supply and isolation unit 184 could comprise an isolation transformer to ensure that no voltage spikes from the AC source 182 could reach the patient. The "safe" DC power from the DC power supply and isolation unit 184 can then go into a power management and reset controller 186 to drive a battery charger 188 that charges a battery 190 and/or goes through a voltage regulator 192 to power the ferromagnetic object detector (100 in FIG. 1A or 110 in FIG. 1B).

The system of FIG. 8 could be configured without an external alternating current source 182. In this case, the DC power supply and isolation module 184 and power management and reset controller 186 would not be needed. The battery charger 188 would also not be needed or it could be external to the system. The system could then operate directly off the battery 190 and voltage regulator 192.

The battery 190 could be any battery capable of being understood by anyone skilled in the art. In one embodiment, the battery is a lithium battery, and more specifically a lithium polymer battery that is rechargeable. The voltage regulator 192 could be any voltage regulator capable of being understood by anyone skilled in the art. In one embodiment, the voltage regulator has a DC output voltage of 3.3 Volts.

Light signals from the probe handle LEDs 124, the system controller LEDs 166, visual cues on the display screen 162 could be of varying colors and different shapes to locate ferromagnetic objects providing proximity and direction. Audible signals from the speaker 154 could also be varying in intensity to provide proximity to ferromagnetic objects, and generate alerts and alarms. The display screen 162 could show an intensity signal as well as direction and count of the ferromagnetic items. The system could have sensitivity controls. The probe shaft 110 could have telescoping features and a steerable tip.

Referring to FIG. 8 in conjunction with FIG. 1B, the functions shown for the system controller 140 and probe handle 120 in FIG. 1A could all be in the combined probe handle and system controller, shown at 142 in FIG. 1B. Referring to FIG. 8 in conjunction with FIG. 1A and FIG. 1B, the power source and receiving unit could be directly attached to the probe shaft 110 or connected via cable. For a cable-connected unit, the power source could be a standard 110/240-volt wall outlet.

Referring to FIG. 8, the probe shaft 110 could be a unit that is user attachable to the probe handle 120. Thus, different probe shafts 110 could be attached at different times, which would allow the probe shaft to be a pre-sterilized disposable unit, separate from the rest of the system. User-detachability of the probe shaft would also allow different types of probe shafts to be attached for different applications. These alternative probe shafts will be discussed later in this document.

Figure 9:
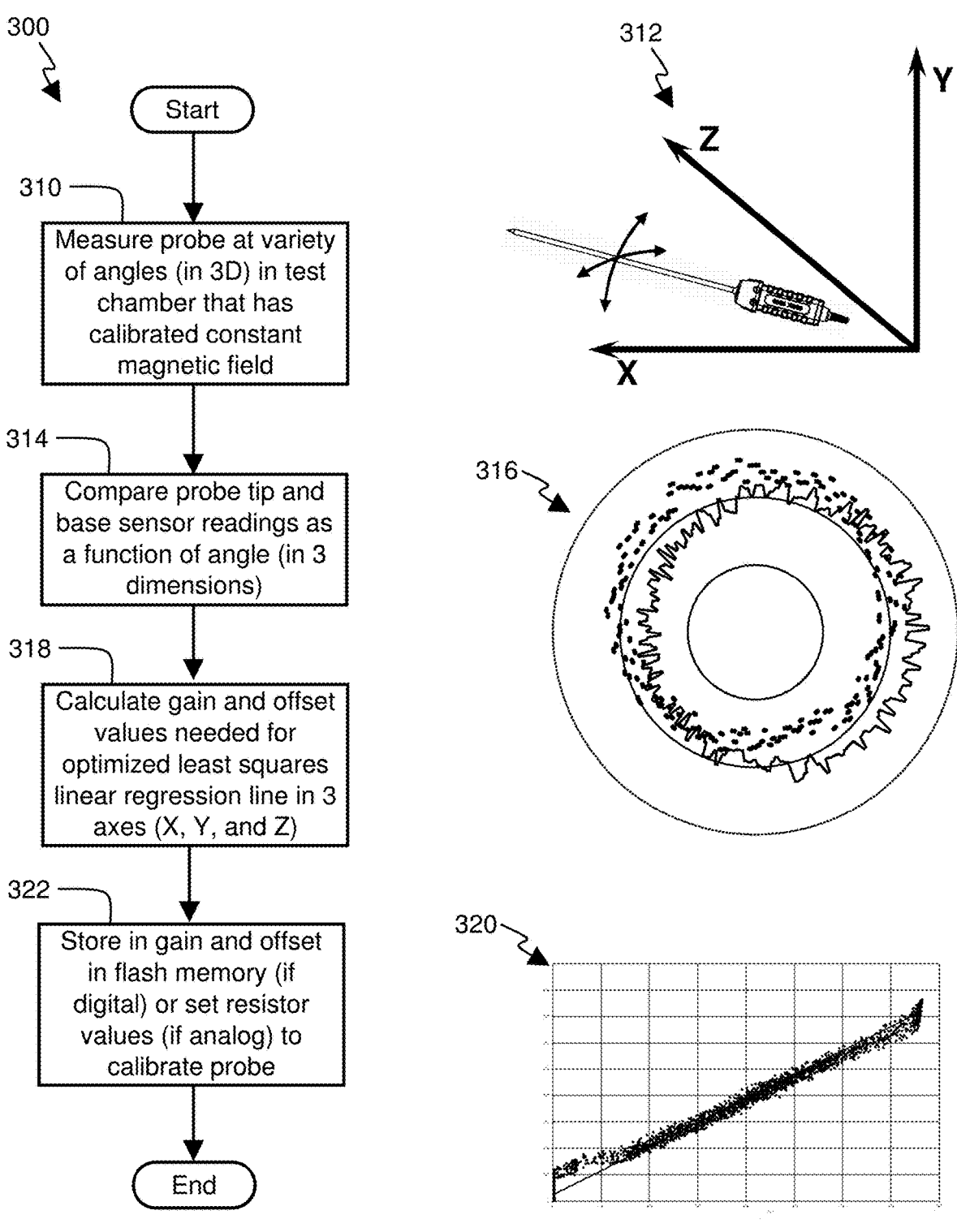
FIG. 9 shows a method for calibrating the system of FIG. 1A to FIG. 8.

FIG. 9 shows a method for factory calibrating the X, Y, and Z axis digital offset and gain values that were shown at 240X, 240Y, 240Z, 241X, 241Y, and 241Z in FIG. 7. Referring to FIG. 9, the calibration method, shown at 300, comprises the following steps:

(a) Measuring probe tip and probe base sensor module readings (the values shown at 240X, 240Y, 240Z, 241X, 241Y, and 241Z in FIG. 7) at a variety of angles in a calibrated magnetic field, as shown at 310, and visually depicted at 312;

(b) Comparing the probe tip and probe base sensor module readings (shown as 238X, 238Y, 238Z, 239X, 239Y, and 239Z in FIG. 7) as shown at 314, and visually depicted at 316;

(c) Calculating the gain and offset values needed for an optimized least squares linear regression line in 3 axes, as shown at 318 and visually depicted for one axis at 320; and (d) Storing these gain and offset values in a non-volatile memory as shown at 322. Note that if the sensor modules produced analog outputs instead of digital outputs, the gain and offset for the sensor modules could be set using resistor values.

Note that 316 in FIG. 9 depicts a 2-dimensional polar plot in which the probe tip readings are shown as dots and the probe base readings are shown as a connected set of lines. This polar plot can be used to adjust the gain and offsets in two axes (for example X and Y) for the two sensors. The process must be repeated in the Z-axis and would ideally be performed in both the XZ plane and the XY plane in step 314 of the process shown at 300 in FIG. 9.

Note that 310 in FIG. 9 depicts a linear regression for one probe tip in one axis. This linear regression must be performed for each of three axes for each of the two sensor modules for a total of six linear regressions.

Further referring to FIG. 7 in view of FIG. 9, it should be noted that the signals picked up by the magneto-resistance sensor modules are inherently noisy as a result of various types of interference, including electromagnetic interference. By taking a large number of readings and averaging these over a longer time period, it becomes possible to distinguish an actual difference in a magnetic field caused by a ferromagnetic object in a body cavity from ambient magnetic fields.

Figure 10:
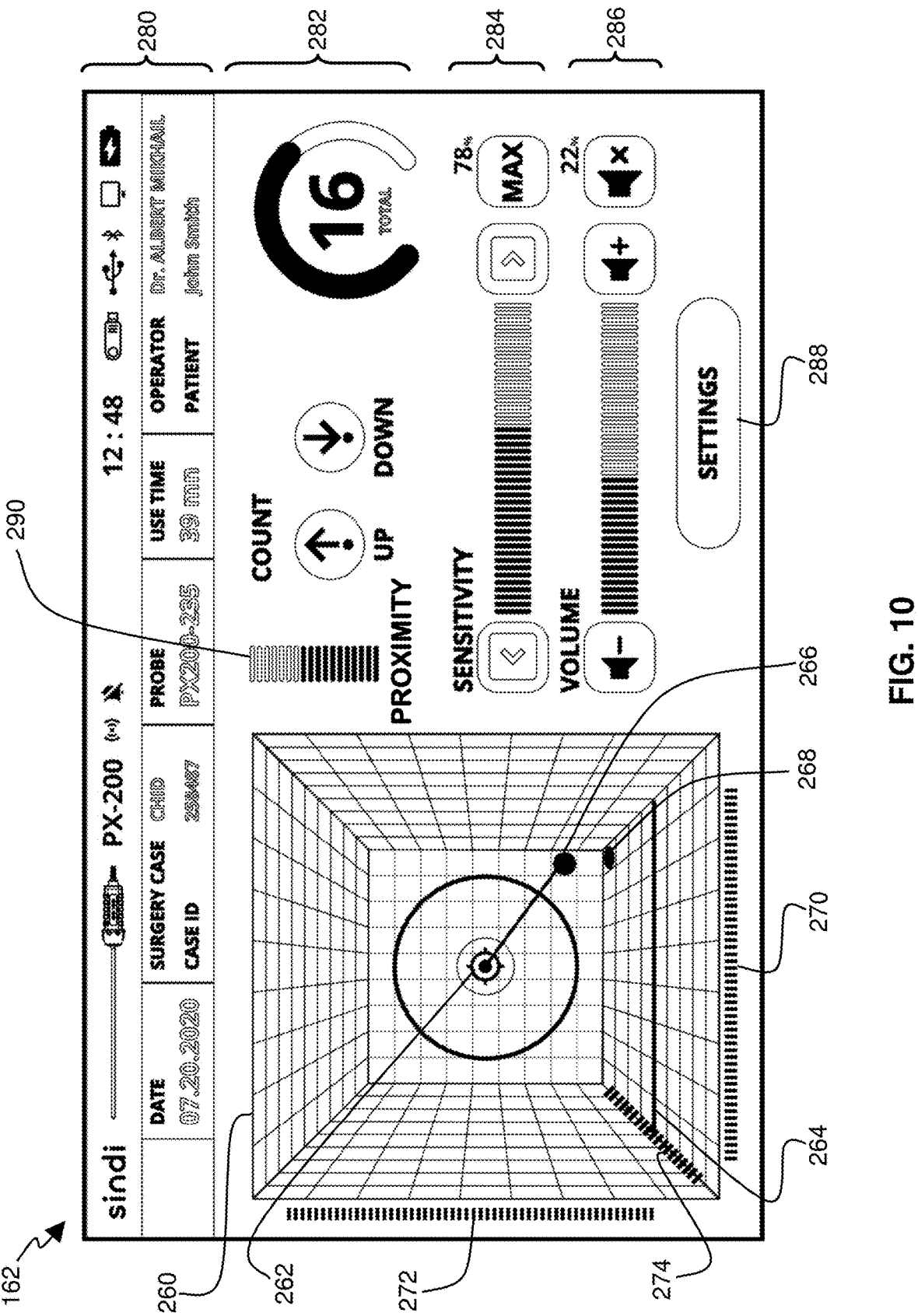
FIG. 10 shows information displayed by the system of FIG. 1A to FIG. 8.

FIG. 10 shows an example of the content of the display screen 162 that was referred to and discussed with reference to FIG. 8, and is part of the system controller 140 shown in FIG. 1A, FIG. 1C, FIG. 2, and FIG. 8. The two-dimensional display screen 162 can comprise a simulated three-dimensional perspective of the spatial relationship of the probe tip and a detected ferromagnetic object as shown at 260. This simulated 3D perspective 260 can be thought of as representing a cubic volume in which deeper objects become smaller, as shown by the converging perspective lines on the top, bottom and sides of the simulated cubic volume. The simulated 3D perspective 260 can comprise a probe tip position indicator, shown at 262, and a detected ferromagnetic object position indicator, shown at 266.

In the embodiments shown in FIG. 10 and FIG. 11A to FIG. 11F, the probe tip position indicator 262 is always in the center of the simulated cubic volume on the left-right (horizontal) axis 270, the up-down (vertical) axis 272, and the in-out (depth) axis 274. The central plane of the cubic volume on the in-out axis is identified by a thick horizontal line 264 on the bottom plane of the simulated 3D perspective. The probe tip position indicator 262 is always shown in the middle of the cubic volume above this horizontal line 264. The probe tip position indicator 262 always stays the same size.

Figures 11A, 11B, 11C, 11D, 11E, 11F:
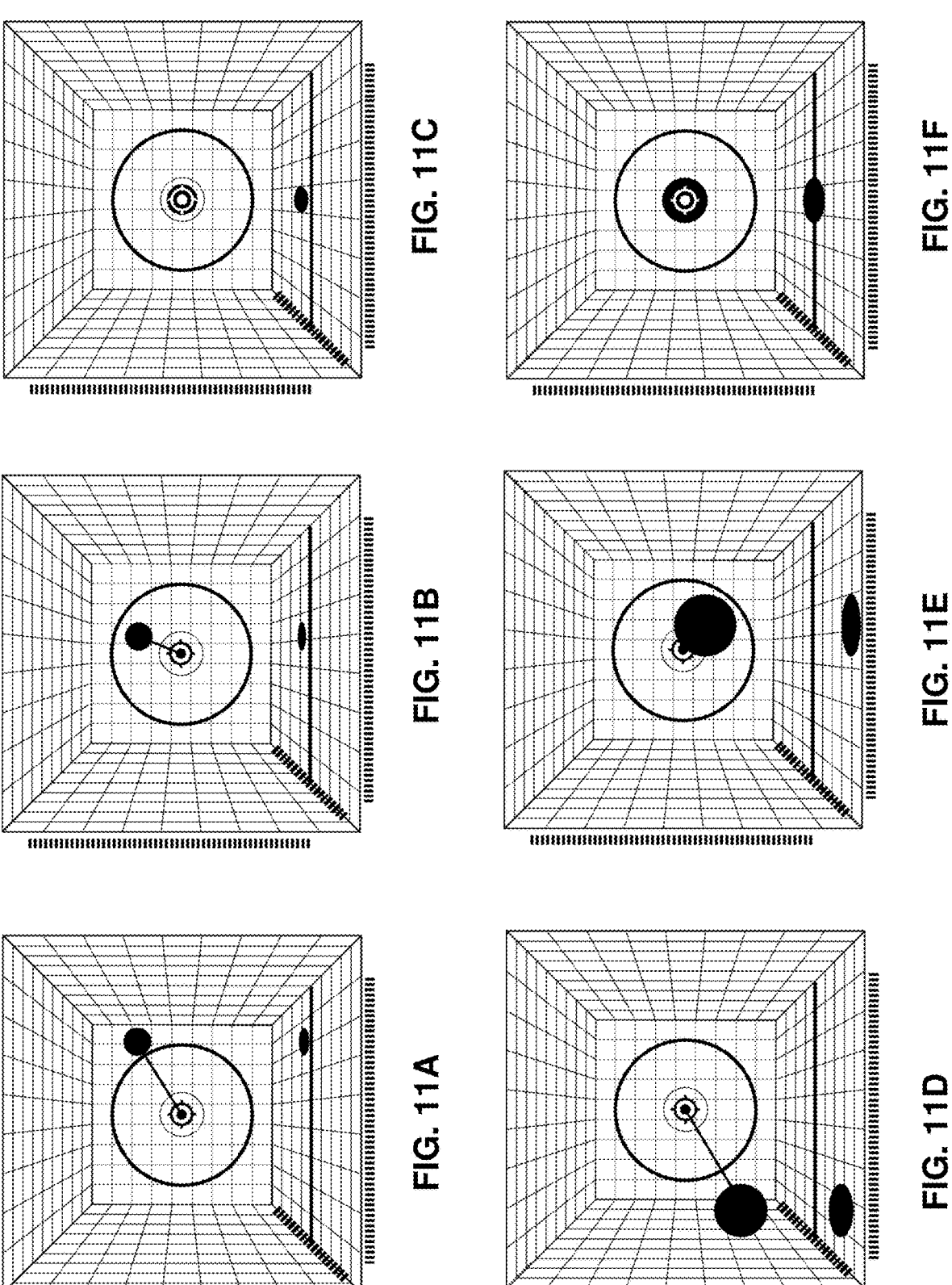
FIG. 11A to FIG. 11F show the 3-dimensional display of FIG. 10 for different positional relationships between the probe tip and ferromagnetic object.

In the embodiments shown in FIG. 10 and FIG. 11A to FIG. 11F the horizontal and vertical position of the detected ferromagnetic object is shown relative to the probe tip. To show relative depth, the detected ferromagnetic position indicator 266 increases and decreases in size depending upon the depth of the detected ferromagnetic object relative to the depth of the probe tip. To further show depth, the ferromagnetic object position is also projected onto the base of the simulated cubic volume, as shown at 268. Thus, the user can compare the location of the projected ferromagnetic object position 268 to the horizontal line showing the central depth plane of the probe tip 264 to determine whether the probe tip should be moved in or out. As examples:

FIG. 10 shows a detected ferromagnetic object that is further into the body of a patient, and further to the right and further down, than the probe tip;

FIG. 11A shows a detected ferromagnetic object that is approximately at the same depth as the probe tip, further to the right and slightly further up;

FIG. 11B shows a detected ferromagnetic object that is at approximately the same depth as the probe tip and approximately at the same location as the probe tip, but slightly further up;

FIG. 11C shows a detected ferromagnetic object that is slightly further in, but otherwise aligned with the probe tip;

FIG. 11D shows a detected ferromagnetic object that is further out, further to the left, and further down from the probe tip;

FIG. 11E shows a detected ferromagnetic object that is further out, but otherwise almost exactly aligned with the probe tip; and FIG. 11F shows a detected ferromagnetic object that is at the same location as the probe tip.

In an alternative embodiment of the display screen, the size of the diameter of the circle representing the detected ferromagnetic object could enlarge with proximity of the detected ferromagnetic object to the probe tip. Embodiments of the display could also comprise a light meter, shown at 290, in the form of a bar graph that changes length and color to represent proximity of the detected ferromagnetic object to the probe tip.

The display screen in FIG. 10, and FIG. 11A to FIG. 11F is shown in black and white. It can be appreciated that embodiments of the invention could have color displays and that color can be used to provide information of the location of a detected ferromagnetic object relative to the probe tip. For example, red could be used to indicate a ferromagnetic object that is far away, green could be used to indicate a detected ferromagnetic object that is close by and intermediate rainbow colors such as orange and/or yellow could be used for ferromagnetic objects that are at an intermediate range from the probe tip.

The display screen 162 shown in FIG. 10 can also provide surgical procedure information, as shown at 280. This surgical procedure data 280 can comprise:

Information describing which probe shaft is attached;
Time and date information;
Surgical case information;
Operator information; and
Patient information.

The display screen 162 shown in FIG. 10 can further comprise touchscreen functionality and this touchscreen functionality can be used to perform and get visual feedback on functionality such as:

(a) A manually entered count of the quantity of ferromagnetic objects detected, as shown at 282;

(b) An adjustment of sensitivity for detecting ferromagnetic objects, as shown at 284;

(c) An adjustment of the audio volume that is emitted by the system when a ferromagnetic object is detected, as shown at 286; and (d) The ability to go to other screens to input data and/or change configurations, as shown at 288.

6. Alternate Embodiments With Additional Magnetoresistance Sensors

Figure 12:
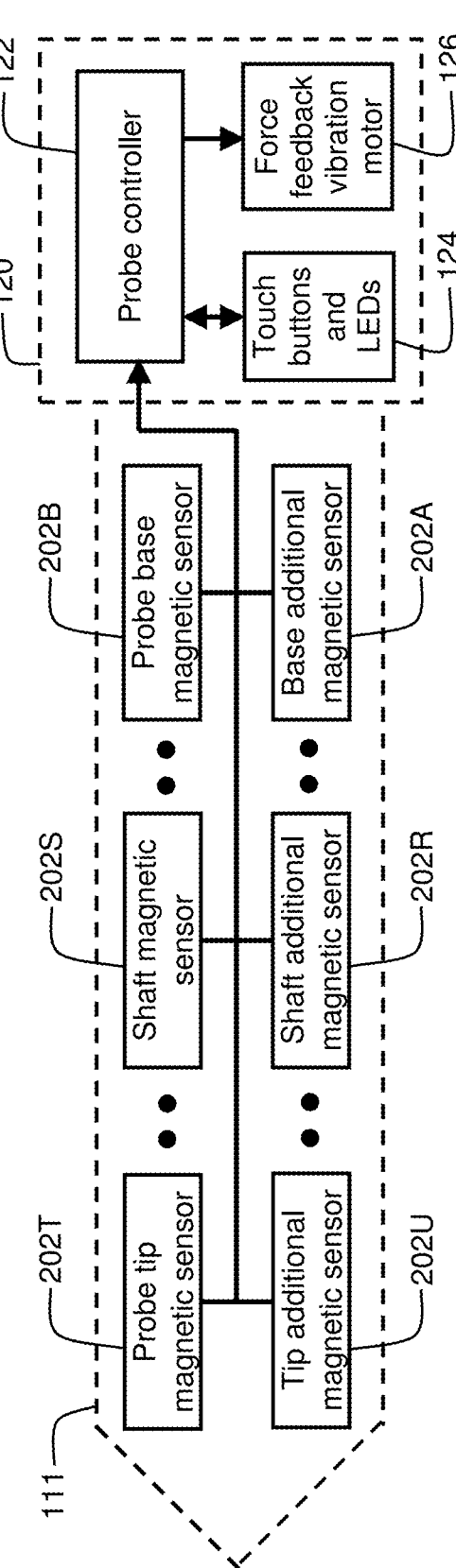
FIG. 12 shows a configuration of an alternate magnetic probe that has more than two magnetic sensors and can be used for pre-MRI detection of ferromagnetic objects.

FIG. 12 shows a configuration of an alternate magnetic probe shaft 111 that has more than two magnetic sensors. It can be understood that the alternate probe shaft 111 in FIG. 12 attaches to the same probe handle 120 that was shown in FIG. 8 and this probe handle 120 also comprises the same probe controller 122, touch buttons and LEDs 124, and force feedback motor 126. The alternate probe shaft 111 comprises the probe tip magnetic sensor 202T and probe base magnetic sensor 202B that were shown for the probe shaft 110 of FIG. 8. The alternative probe shaft 111 further comprises an additional probe base magnetic sensor, shown at 202A, an additional probe tip magnetic sensor, shown at 202U, a probe shaft magnetic sensor, shown at 202S, and an additional probe shaft magnetic sensor shown at 202R. The probe shaft magnetic sensors (202R and 202S) are located at an intermediate point along the probe shaft, between the probe tip sensors (202T and 202U) and the probe base sensors (202A and 202B). These additional magnetic sensors (202A, 202U, 202R, and 202S) could comprise the same elements and functionality that has been described for the probe tip magnetic sensor 202T and the probe base magnetic sensor 202B. One or more of these additional magnetic sensors (202A, 202U, 202R, and 202S) could improve the capability for the system to (a) more precisely locate a ferromagnetic object, (b) to simultaneously discriminate between multiple ferromagnetic objects, and/or(c) to more rapidly scan a large region. A system using the alternate probe shaft 111 having three or more magnetic sensors could therefore also be effectively used for non-surgical applications, such as an external scan of a patient's body prior to an MRI (magnetic resonance imaging) scan, to ensure that the patient's body has no ferromagnetic objects that could create harm, by for example, heating of the ferromagnetic object within the living organism's body.

Figures 13A, 13B:
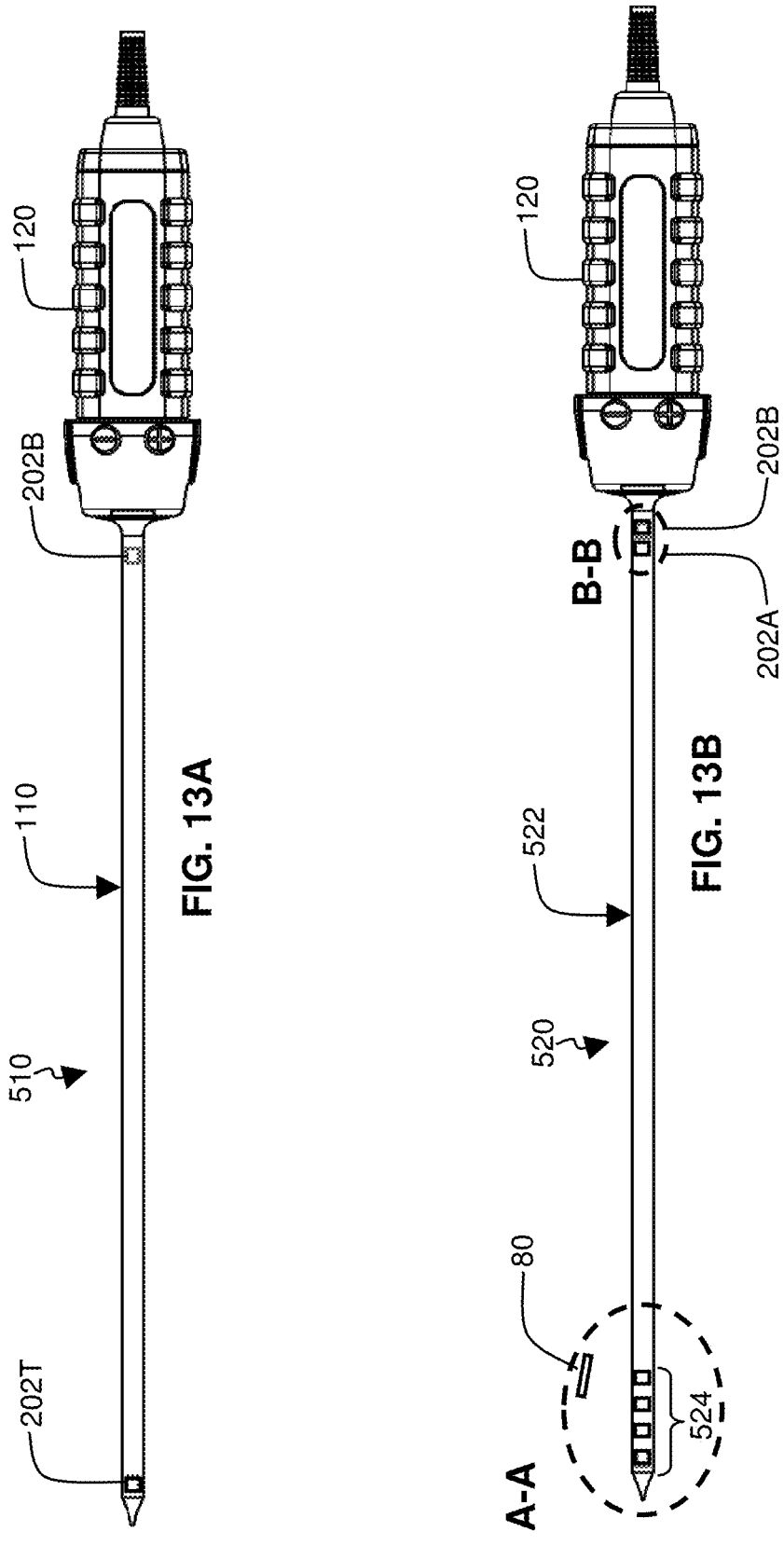
FIG. 13A shows a medical ferromagnetic object detector having a single magnetoresistance module at the probe tip and at the probe base.
FIG. 13B shows ferromagnetic object detector having a plurality of magnetoresistance modules at the probe tip and two magnetoresistance modules at the base.

FIG. 13A to FIG. 13B show alternative configurations of the sensors incorporated in the medical ferromagnetic object detectors that have been shown and described earlier in this document. More specifically, FIG. 13A shows a medical ferromagnetic object detector 510 comprising a probe handle 120 and a probe shaft 110 where the probe shaft 110 comprises one probe tip three axis magnetoresistance module 202T and one probe base three axis magnetoresistance module 202B. These components and their functions as part of a medical ferromagnetic object detector were previously illustrated and/or described with reference to FIG. 1A, FIG. 1B, FIG. 1C, FIG. 2, FIG. 6. FIG. 7, and FIG. 8, as well as other previous sections of this document.

FIG. 13B shows an alternate ferromagnetic object detector 520 that comprises an alternative probe shaft 522. This alternate embodiment of a probe shaft 522 comprises two probe base three-axis magnetoresistance modules, 202B and 202A. These could specifically be identified as a first probe base three-axis magnetoresistance module 202B, and a second (or additional) probe base three-axis magnetoresistance module 202A. The probe base three-axis magnetoresistance modules 202A and 202B were previously shown and described with respect to FIG. 12. This alternate embodiment probe shaft 522 also comprises a linear array of probe tip three-axis magnetoresistance modules 524, that comprises four sensors (202T, 202U, 202V, and 202W individually labeled in FIG. 14A). The sensors in the linear probe tip three-axis magnetoresistance module array 524 are aligned with the axis of the alternate probe shaft 522. By averaging the signals from the three-axis magnetoresistance modules in the array 524, and comparing the results of these averages in three orthogonal axes (X, Y, and Z) with the average signal in the X, Y, and Z orthogonal axes for the two sensors at the probe base 202A and 202B, it is possible to get a more accurate signal difference to help detect and locate a ferromagnetic object, such as the object shown at 80 in FIG. 13B, that was previously shown in FIG. 3.

The sensors in the probe tip array 524 of FIG. 13B are horizontally separated. Magnetic field strength decreases as the cubic power of distance from a magnetic object. Similarly, the distortion of a magnetic field caused by a ferromagnetic object (such as 80 in FIG. 13B) decreases by the cubic power of distance from the ferromagnetic object. Thus, in a system not affected by any other factors, the following equations can be used to determine the distance from a tip sensor to a ferromagnetic object:

$$E = K/d^3$$

$$d = (E/K)^{(1/3)}$$

Where:

E=the distortion in the magnetic signal caused by the ferromagnetic object, which can also be expressed as the difference in the magnetic signal at the tip sensor and the base sensor (or average of multiple base sensors);

d=the distance between the tip sensor and the ferromagnetic object; and

K=a constant based on properties of the ferromagnetic object and the magnetic sensor.

Figures 14A, 14B:
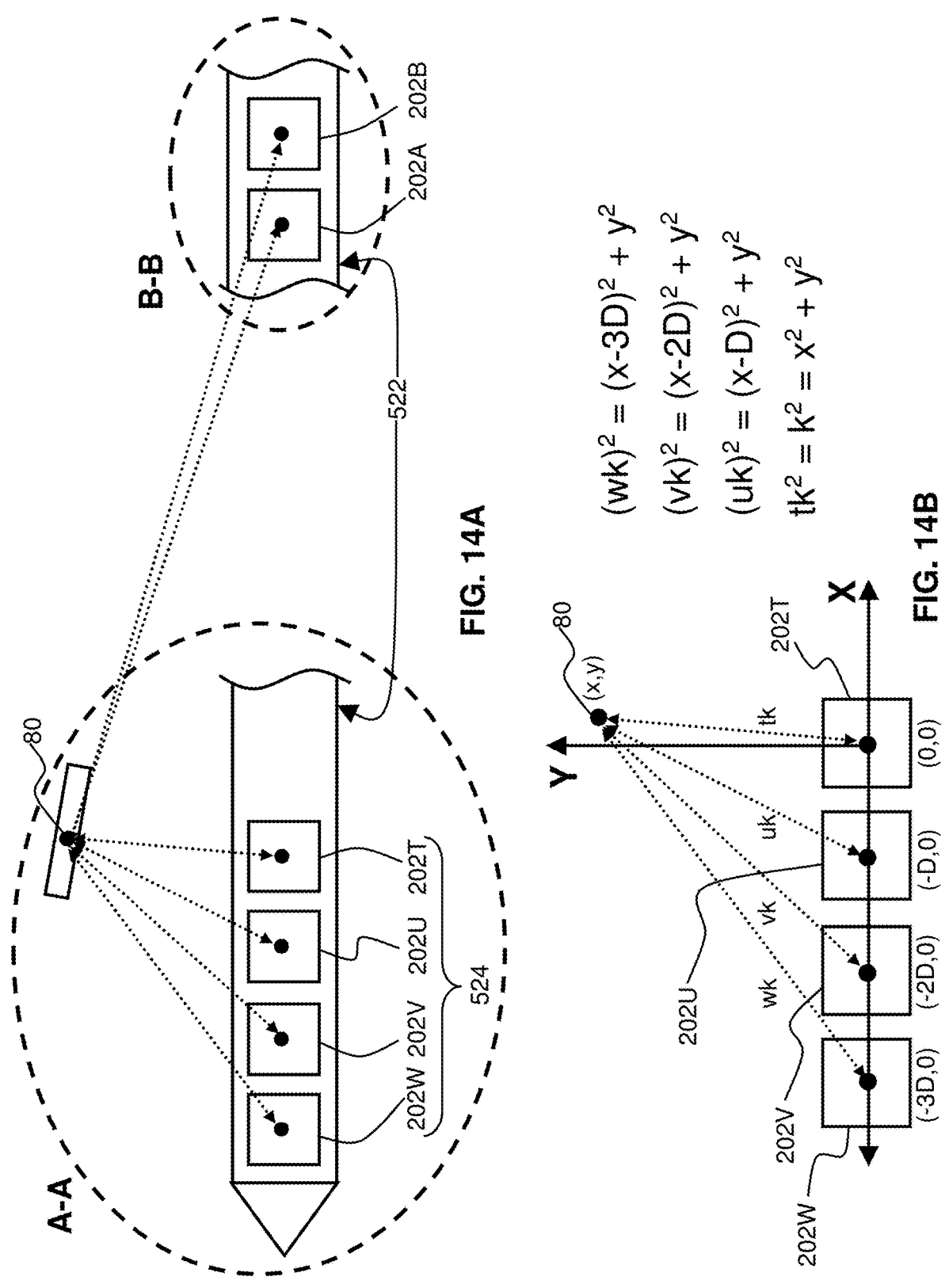
FIG. 14A shows details of region A-A and region B-B of FIG. 13B.
FIG. 14B shows a two-dimensional example of how the relative distance information from the sensor output of the embodiment shown in FIG. 13B and FIG. 14A can be used to calculation the location of a ferromagnetic object.

FIG. 14A is a close-up of a ferromagnetic object proximate to region A-A of FIG. 13B to illustrate a two-dimensional example of how the linear array of tip sensors 524 (comprising 202T, 202U, 202V, and 202W) of the alternate embodiment ferromagnetic object detector 520 of FIG. 13B can be used to more precisely locate the ferromagnetic object 80 using the distance equation provided above. Also shown in FIG. 14A are the base sensors 202A and 202B in region B-B of FIG. 13B on the distal end of the probe shaft 522. The base sensors, 202A and 202B, can be considered to be so far away from the ferromagnetic object 80 that there is no distortion of the ambient magnetic field caused by the ferromagnetic object. For this example, the two-dimensional angle (in degrees) of the measured magnetic field at each of the four tip sensors and the two base sensors is as follows:

| | Sensor | | | | | |
| --- | --- | --- | --- | --- | --- | --- |
| | 202W | 202V | 202U | 202T | 202A | 202B |
| Measured angle | 57.78 | 58.19 | 58.91 | 59.32 | 57.32 | 57.34 |
| Average base angle | — | — | — | — | 57.33 | |
| Angular distortion | 0.45 | 0.86 | 1.58 | 1.99 | | |

To understand these multi-sensor systems, it is important to recognize that the distortion of an ambient magnetic field caused by a ferromagnetic object is a function of the following factors:

(a) The size of the object;

(b) The shape of the object;

(c) The orientation of the object; and (d) The material the object is made from; and (e) The inverse cube of the distance between the object and the sensor.

In FIG. 14A and FIG. 13B all sensors are looking at the same ferromagnetic object 80, which means that size, shape, orientation, and material are the same. Thus, we can use the relative differences in angular distortion of the ambient magnetic field to calculate the inverse cube of the distance from each sensor to the ferromagnetic object. For simplicity, we will normalize the angular distortions by dividing by the largest distortion so that the largest normalized value is 1. Based on the foregoing equations, the normalized angular distortions (E) will be equal to $K/d^3$, which can then be converted to relative distances (kd) from each of the sensors to the ferromagnetic object as shown below. Note that this can most easily be done by defining a new constant k, where $k = K^{(-1/3)}$). Also note that these resulting calculated values (W, V, U, and T) below are then the individual relative distances to each sensor, which could also be written as wk, vk, uk, and tk.

| | 202W | 202V | 202U | 202T |
| --- | --- | --- | --- | --- |
| Angular distortion | 0.45 | 0.86 | 1.58 | 1.99 |
| Normalized to largest value ($K/d^3$) | 0.226 | 0.432 | 0.794 | 1.000 |
| Invert previous row ($d^3/K$) | 4.422 | 2.314 | 1.259 | 1.000 |
| Cube root of previous row (kd) | 1.641 | 1.323 | 1.080 | 1.000 |
| | (W = wk) | (V = vk) | (U = uk) | (T = tk) |

Once these calculations have been made, it is possible to calculate the location of the ferromagnetic object 80 using trigonometry as shown in FIG. 14B. Specifically, FIG. 14B shows the same detail for region A-A that was shown in FIG. 14A, placed onto an XY coordinate system having an origin at the center of sensor 202T. The four probe tip sensors and their midpoints shown at 202W, 202V, 202U, and 202T. The detected ferromagnetic object is at a location specified by two unknown variables labeled as lower-case x and lower-case y. If the four probe tip sensors (202W, 202V, 202U, and 202T) are equally spaced from each other on the X-axis and the spacing distance between each probe tip sensor is a distance D, then the locations of each of the probe tip sensors can be expressed as follows and as shown in FIG. 14B:

Sensor 202T is at the origin: (0,0)

Sensor 202U is one increment (D) to the left of 202T, which is at the origin: (–D,0)

Sensor 202V is two increments (2D) to the left of 202T, which is at the origin: (–2D,0)

Sensor 202W is three increments (3D) to the left of 202T, which is at the origin: (–3D)

Based on the X-Y coordinate system shown in FIG. 14B, the location of the center (x,y) of the detected ferromagnetic object 80 can be calculated relative to each of the four sensors (202W, 202V, 202U, and 202T) using the Pythagorean theorem:

The hypotenuse is the distance between each sensor and the detected object as calculated in the table above (wk, vk, uk, and tk).

The distance in the X-direction is x plus the X-coordinate for each of the sensors as given in the list above (x for 202T, x–D for 202U, etc.).

The Y-distance in all cases is y.

This results in the following equations:

$$(wk)^2=(x-3D)^2+y^2$$

$$(vk)^2=(x-2D)^2+y^2$$

$$(uk)^2=(x-D)^2+y^2$$

$$(tk)^2=x^2+y^2$$

This results in four equations representing the four sensor locations. By setting the equations up in this way, the value for the variable t for the sensor closest to the ferromagnetic object is 1, because normalized all values based on this value being 1 in the table above. Thus, there are four equations and only three unknowns (x, y, and k). The extra equation can be used to improve the accuracy of the result or to provide error bounds. For the example values given, and a spacing (D=5 mm) between the sensors these equations would be:

$$((1.641)(k))^2=(x-(3)(5))^2+y^2$$

$$((1.323)(k))^2=(x-(2)(5))^2+y^2$$

$$((1.080)(k))^2=(x-5)^2+y^2$$

$$k^2=x^2+y^2$$

The above four equations can then be reduced to three equations with two unknowns by substituting for $k^2$. This gives the following three equations for our example values, any pair of which can be used to solve for x and y using numerical methods, capable of being understood by anyone skilled in the art:

$$((1.641)^2(x^2+y^2)=(x-(3)(5))^2+y^2$$

$$((1.323)^2(x^2+y^2)=(x-(2)(5))^2+y^2$$

$$((1.080)^2(x^2+y^2))=(x-5)^2+y^2$$

Figures 15A, 15B, 15C:
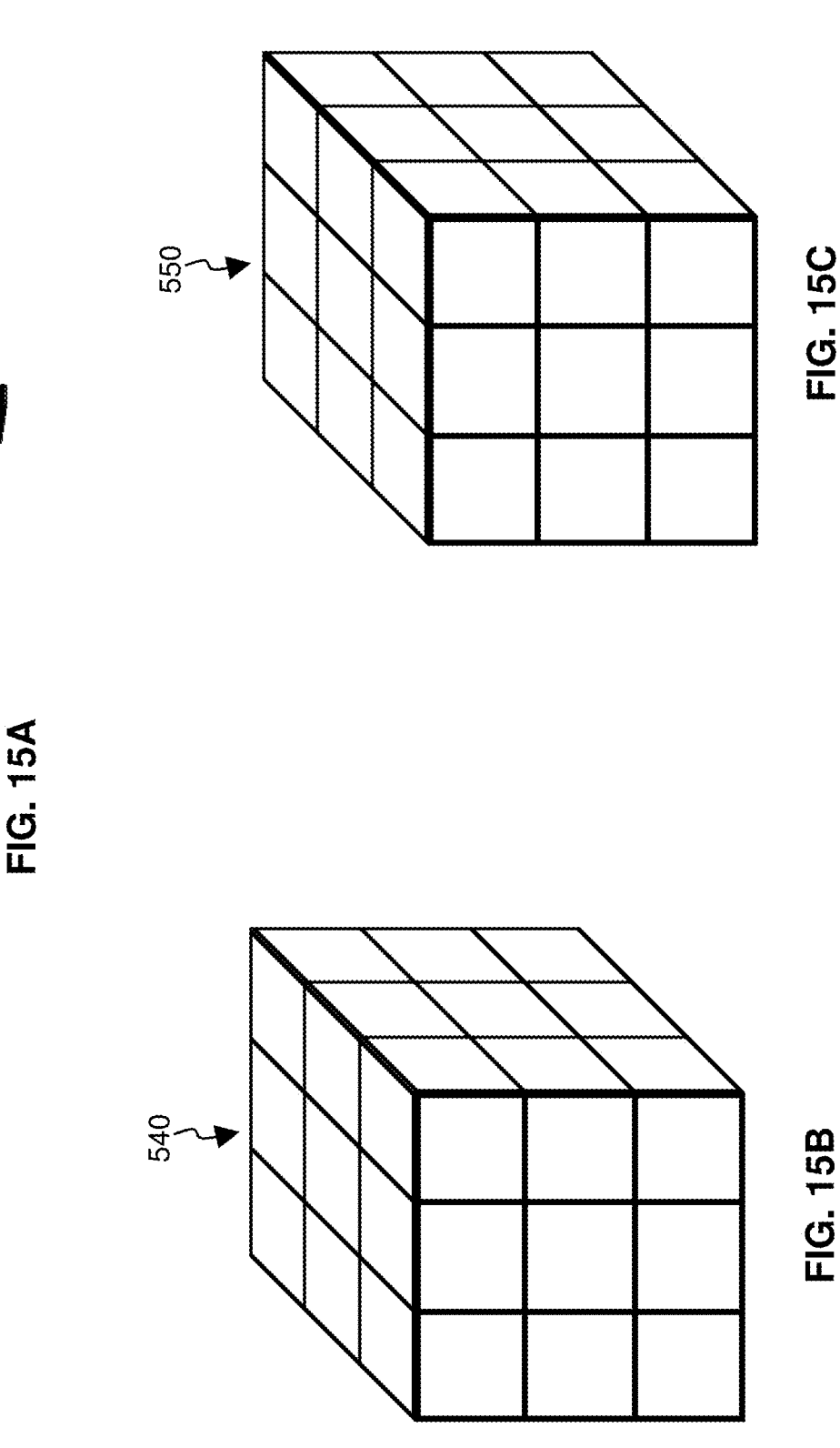
FIG. 15A shows a ferromagnetic object detector having a three-dimensional array of magnetoresistance modules at the probe tip and at the probe base.
FIG. 15B and FIG. 15C show enlarged views of the probe tip sensing array and the probe base sensing array of FIG. 15A.

It should be noted that the concepts shown in the two-dimensional example shown in FIG. 13B, FIG. 14A, and FIG. 14B that uses as linear array of probe tip sensors, can also be applied to devices that have sensors distributed in more than one dimension to find ferromagnetic objects in all three dimensions. For example, FIG. 15A shows another alternative ferromagnetic object detector 530 comprising another alternative probe shaft 532 that has a probe tip three-dimensional array of three-dimensional magnetoresistance modules 540 and a probe base three-dimensional array of three-dimensional magnetoresistance modules 550. The three-dimensional probe tip sensor array 540 in the embodiment shown in FIG. 13C is conceptually similar to the one-dimensional sensor array 524 in the embodiment shown in FIG. 13B, but instead of having a distribution of three-dimensional magnetoresistance modules aligned along one axis, the embodiment in FIG. 13C has the modules distributed in three axes to provide even further benefits in (a) redundantly reading the angular distortion of the magnetic field, and (b) precisely locating a ferromagnetic object. The same applies to the use of a three-dimensional array of three-dimensional magnetoresistance sensors in the base 550 instead of the pair of three-dimensional sensors 202A and 202B in the embodiment shown in FIG. 13B. FIG. 15B and FIG. 15C shows enlarged views of the probe tip and probe base sensing arrays of FIG. 15A. In this case, both arrays are 3×3×3 arrays with all sensors equally spaced in three orthogonal axes.

Figures 16A, 16B:
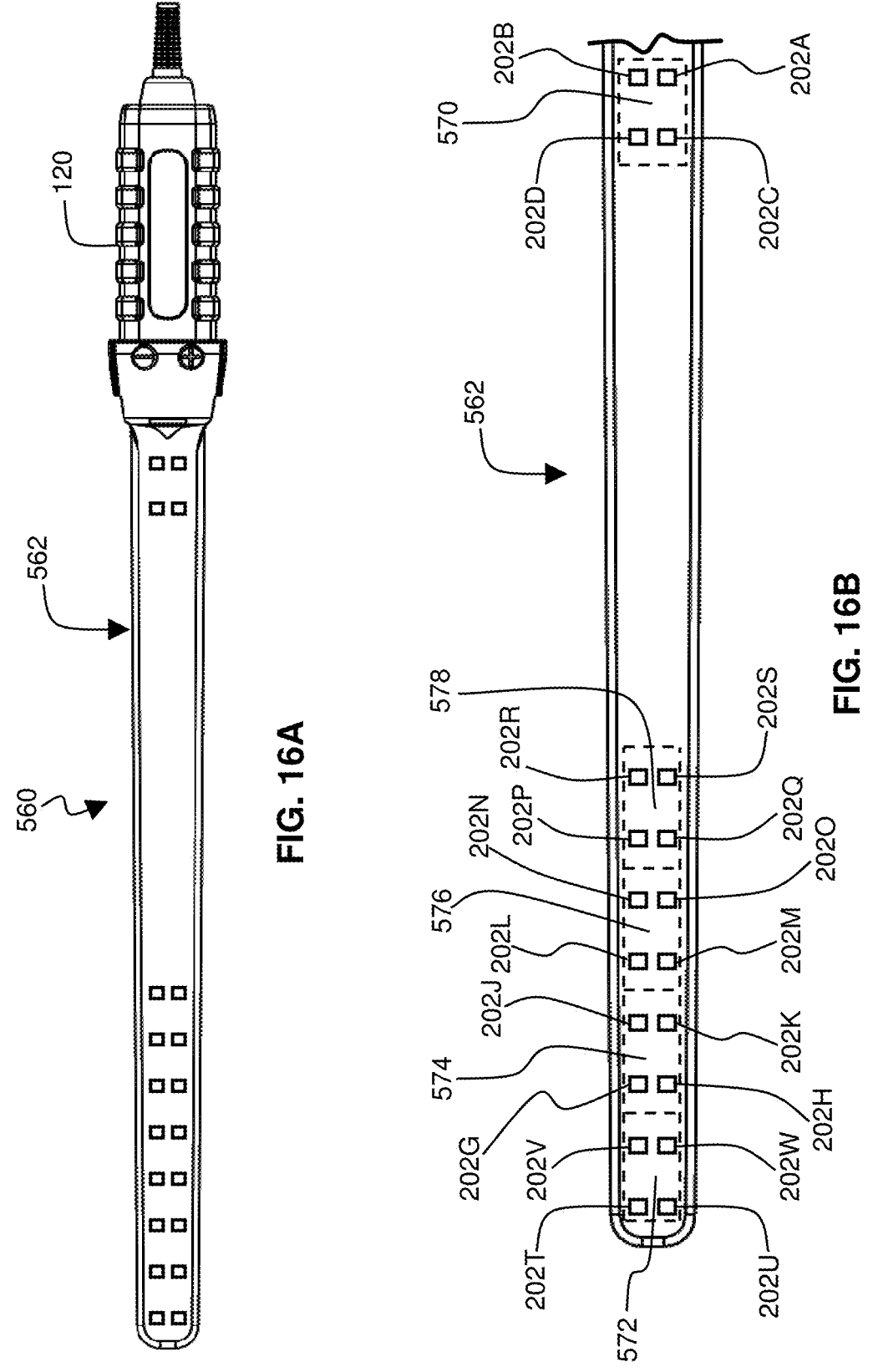
FIG. 16A and FIG. 16B show a ferromagnetic object detector with magnetoresistance modules distributed along a two-dimensional plane of the probe shaft and the use of zone-based sensing.

FIG. 16A shows yet another alternative ferromagnetic object detector 560 comprising yet another alternative probe shaft 562 that comprises three-dimensional magnetoresistance sensor modules distributed along the length and width of a two-dimensional plane of the probe shaft 560. FIG. 16B is a close-up view of the planar probe shaft 462 of FIG. 16A. The planar probe shaft of FIG. 16A and FIG. 16B comprises:

(a) A 2×2 planar array of probe base magnetic sensor modules shown at 202A, 202B, 202C, and 202D, and collectively labeled as 570;

(b) A 2×2 planar array of probe tip magnetic sensor modules shown at 202T, 202U, 202V, and 202W, and collectively labeled as 572; and (c) A planar array of probe shaft magnetic sensor modules shown at 202G, 202H, 202J, 202K, 202L, 202M, 202N, 202O, 202P, 202Q, 202R, and 202S that are grouped into three zones shown at 574, 576, and 578.

The magnetic sensor modules shown in FIG. 16A and FIG. 16B can be used for zone-based sensing that further improves accuracy and detection range by averaging the signals for each set of sensors in a zone (270, 272, 274, 276, and 278) and then uses these averages to determine a sensor location using the principles that were described with reference to FIG. 14A and FIG. 14B. Such a probe shaft 462, when coupled with an appropriate averaging and distance finding system as described herein has the potential for being sensitive enough to prove a sensing distance that can be used for non-invasive scanning of a body prior to an MRI scan.

In summary, the following table compares the embodiments shown in FIG. 13A, FIG. 13B, FIG. 15A, and FIG. 16A.

|  | FIG. 13A | FIG. 13B | FIG. 15A | FIG. 16A |
|---|---|---|---|---|
| Application example | Post-surgical retained ferromagnetic object detection and location | Post-surgical retained ferromagnetic object detection and location | Post-surgical retained ferromagnetic object detection and location | Pre MRI body scan for ferromagnetic objects |

-continued

|  | FIG. 13A | FIG. 13B | FIG. 15A | FIG. 16A |
|---|---|---|---|---|
| Improvements over FIG. 13A embodiment | Not applicable | Redundancy improves resolution. Spatial separation improves ability to accurately locate object | Redundancy improves resolution. Spatial separation improves ability to accurately locate object | Usable external to the body. Can scan body faster and determine location more easily |

7. Fields of Use

Examples of fields of use for embodiments of the present invention can include, but are not limited to:

a. Detection of retained foreign ferromagnetic objects during or after surgery;

b. Location of objects with a ferromagnetic material added to make them detectable during or after surgery;

c. Detection of items in a human or animal body that are not safe for use with magnetic resonance imaging (MRI) machines; and d. Detection of fragments of shrapnel, etc. that are ferromagnetic.

Embodiments of the present invention could be used in conjunction or as part of a device for extracting foreign objects from a patient. Embodiments of the present invention could be used in conjunction with other detection devices that use ultrasound for example, to image and help the foreign object detection, identification, and extraction process. Embodiments of the present invention could be configured and/or used for conventional open surgery as well as minimally invasive surgical procedures in or outside the patient's body cavity for both human and animal procedures.

A number of variations and modifications of the disclosed embodiments can also be used. While the principles of the disclosure have been described above in connection with specific apparatuses and methods, it is to be clearly understood that this description is made only by way of example and not as limitation on the scope of the disclosure.

What is claimed is:

1. A system for displaying a location of a ferromagnetic object in a living organism, comprising:

a probe shaft with a distal end configured for insertion into the living organism and a proximal end configured for remaining outside the living organism;

a probe tip magnetoresistance module located at the distal end and responsive to an ambient magnetic field in three orthogonal axes at the distal end, wherein the probe tip magnetoresistance module comprises:

a probe tip X-axis magnetoresistance sensor which generates a probe tip X-axis electrical signal in response to the ambient magnetic field;

a probe tip Y-axis magnetoresistance sensor which generates a probe tip Y-axis electrical signal in response to the ambient magnetic field; and a probe tip Z-axis magnetoresistance sensor which generates a probe tip Z-axis electrical signal in response to the ambient magnetic field;

a probe base magnetoresistance module located at the proximal end and responsive to the ambient magnetic field in three orthogonal axes at the proximal end wherein the probe base magnetoresistance module comprises:

a probe base X-axis magnetoresistance sensor which generates a probe base X-axis electrical signal in response to the ambient magnetic field;

a probe base Y-axis magnetoresistance sensor which generates a probe base Y-axis electrical signal in response to the ambient magnetic field; and a probe base Z-axis magnetoresistance sensor which generates a probe base Z-axis electrical signal in response to the ambient magnetic field;

a display configured to show a horizontal, vertical, and depth relationship of the distal end to the ferromagnetic object in a simulated cubic volume based on:

the probe tip X-axis electrical signal;

the probe base X-axis electrical signal;

the probe tip Y-axis electrical signal;

the probe base Y-axis electrical signal;

the probe tip Z-axis electrical signal; and the probe base Z-axis electrical signal.

2. The system as recited in claim 1, wherein:

the probe tip X-axis magnetoresistance sensor comprises a probe tip X-axis tunneling magnetoresistance sensor;

the probe tip Y-axis magnetoresistance sensor comprises a probe tip Y-axis tunneling magnetoresistance sensor;

the probe tip Z-axis magnetoresistance sensor comprises a probe tip Z-axis tunneling magnetoresistance sensor;

the probe base X-axis magnetoresistance sensor comprises a probe base X-axis tunneling magnetoresistance sensor;

the probe base Y-axis magnetoresistance sensor comprises a probe base Y-axis tunneling magnetoresistance sensor;

the probe base Z-axis magnetoresistance sensor comprises a probe base Z-axis tunneling magnetoresistance sensor; and all tunneling magnetoresistance sensors comprise magnetic tunnel junctions comprising two ferromagnetic layers separated by an insulating barrier wherein one of the ferromagnetic layers has a magnetization that does not move in response to an applied magnetic field and the other ferromagnetic layer moves in response to an applied magnetic field.

3. The system as recited in claim 2, wherein:

the display comprises a two-dimensional display;

the horizontal and vertical relationship of the ferromagnetic object is presented as a vertical and horizontal distance between a probe tip visual marker and a ferromagnetic object position indicator on the two-dimensional display; and the relative depth of the detected ferromagnetic object as compared to the location of the probe tip is presented using a visual effect selected from a group of:

a change in size of the ferromagnetic object position indicator on the two-dimensional display; and a projection of the ferromagnetic object position indicator onto the base of a simulated cubic volume on the two-dimensional display.

4. The system as recited in claim 3, wherein:

the distal end of the probe shaft is configured for insertion into an internal cavity of a human through a trocar cannula placed in a body wall of the human as part of a laparoscopic surgical procedure;

the probe tip magnetoresistance module and probe base magnetoresistance modules comprise Wheatstone bridge circuits;

the ferromagnetic object comprises an unintended retained post-surgical foreign body comprising at least one material selected from a group of martensitic stainless steel, nickel, and cobalt;

the system is configured not to be responsive to at least one material selected from a group of austenitic stainless steel, aluminum, and titanium;

the system is further configured to detect the ferromagnetic object in response to a difference between at least one pair of signals selected from a group of:

the probe tip X-axis electrical signal and the probe base X-axis electrical signal;

the probe tip Y-axis electrical signal and the probe base Y-axis electrical signal; and the probe tip Z-axis electrical signal and the probe base Z-axis electrical signal;

the system is configured to generate an alarm in response to the ferromagnetic object wherein the alarm is selected from a group of an audible alarm, a visual alarm, and a haptic alarm;

the system is configured for detecting the ferromagnetic object without generating a magnetic field to detect the ferromagnetic object;

the system further comprises a force feedback vibration motor;

the force feedback vibration motor is responsive to the detection of the ferromagnetic object; and the probe shaft is user attachable and replaceable.

5. The system as recited in claim 1, wherein:

gain and offset of the probe tip X-axis electrical signal, the probe tip Y-axis electrical signal, the probe tip Z-axis electrical signal, the probe base X-axis electrical signal, the probe base Y-axis electrical signal; and the probe base Z-axis electrical signal are configured to be adjusted in response to digital gain and digital offset values stored in a non-volatile memory in the system wherein the digital gain and the digital offset values are determined from a calibration process comprising the steps of:

measuring the probe tip X-axis electrical signal, the probe tip Y-axis electrical signal, the probe tip Z-axis electrical signal, the probe base X-axis electrical signal, the probe base Y-axis electrical signal, and the probe base Z-axis electrical signal at a variety of angles in a calibrated constant magnetic field; and calculating gain and offset values for the probe tip and probe base electrical signals in response to an optimized least squares linear regression calculation of a relationship of the probe tip and probe base electrical signals.

6. The system as recited in claim 1, wherein:

the system comprises a second probe tip magnetoresistance module;

the second probe tip magnetoresistance module comprises a second probe tip X-axis magnetoresistance sensor, a second probe tip Y-axis magnetoresistance sensor, and a second probe tip Z-axis magnetoresistance sensor wherein the second probe tip X-axis magnetoresistance sensor, the second probe tip Y-axis magnetoresistance sensor, and the second probe tip Z-axis magnetoresistance sensor are responsive to an ambient magnetic field in three orthogonal axes at the distal end of the shaft and wherein:

the second probe tip X-axis magnetoresistance sensor generates a second probe tip X-axis electrical signal in response to the ambient magnetic field at the distal end of the shaft;

the second probe tip Y-axis magnetoresistance sensor generates a second probe tip Y-axis electrical signal in response to the ambient magnetic field at the distal end of the shaft; and the second probe tip Z-axis magnetoresistance sensor generates a second probe tip Z-axis electrical signal in response to the ambient magnetic field at the distal end of the shaft; and the display is configured to show the horizontal, vertical, and depth relationship of the distal end to the ferromagnetic object in response to:

the second probe tip X-axis electrical signal;

the second probe base X-axis electrical signal;

the second probe tip Y-axis electrical signal;

the second probe base Y-axis electrical signal;

the second probe tip Z-axis electrical signal; and the second probe base Z-axis electrical signal.

7. The system as recited in claim 1, wherein:

the distal end of the probe shaft is configured for insertion into an internal cavity of a human through a trocar cannula placed in a body wall of the human as part of a laparoscopic surgical procedure.

8. The system as recited in claim 1, wherein:

the display comprises a two-dimensional display;

the horizontal and vertical relationship of the ferromagnetic object is presented as a vertical and horizontal distance between a probe tip visual marker and a ferromagnetic object position indicator on the two-dimensional display; and the relative depth of the detected ferromagnetic object as compared to the location of the probe tip is presented using a visual effect selected from a group of:

a change in size of the ferromagnetic object position indicator on the two-dimensional display; and a projection of the ferromagnetic object position indicator onto the base of a simulated cubic volume on the two-dimensional display.

9. The system as recited in claim 1, wherein:

the system is further configured to detect the ferromagnetic object in response to a difference between at least one pair of signals selected from a group of:

the probe tip X-axis electrical signal and the probe base X-axis electrical signal;

the probe tip Y-axis electrical signal and the probe base Y-axis electrical signal; and the probe tip Z-axis electrical signal and the probe base Z-axis electrical signal.

10. The system as recited in claim 1, wherein:

the system further comprises a force feedback vibration motor; and the force feedback vibration motor is responsive to the detection of a ferromagnetic object.

11. The system as recited in claim 1, wherein:
the probe shaft is user attachable and replaceable.
12. The system as recited in claim 1, wherein:
the system is configured for detecting the ferromagnetic
object without generating a magnetic field to detect the
ferromagnetic object;
the ferromagnetic object comprises an unintended
retained post-surgical foreign body comprising at least
one material selected from a group of martensitic
stainless steel, nickel, and cobalt; and
the system is configured not to be responsive to at least
one material selected from a group of austenitic stain-
less steel, aluminum, and titanium.
13. The system as recited in claim 1, wherein:
the display is configured to show a distance between the
distal end and the ferromagnetic object as a change in
size of an object on the display.
14. The system as recited in claim 1, wherein:
the display further comprises a count of a quantity of
ferromagnetic objects detected.
15. The system as recited in claim 1, wherein:
at least one feature on the display changes color in
response to the
the probe tip X-axis electrical signal;
the probe base X-axis electrical signal;
the probe tip Y-axis electrical signal;
the probe base Y-axis electrical signal;
the probe tip Z-axis electrical signal; and
the probe base Z-axis electrical signal.
16. A ferromagnetic object location visualization system,
wherein:
the system comprises a probe shaft and a display;
the probe shaft comprises:
a probe tip magnetoresistance module located at a distal
end of the probe shaft wherein the probe tip mag-
netoresistance module comprises three orthogonally-
oriented probe tip magnetoresistance sensors config-
ured for:
insertion into a body cavity of a living organism; and
generating three orthogonal probe tip electrical sig-
nals in response to an ambient magnetic field in
the body cavity on said three orthogonally-ori-
ented probe tip magnetoresistance sensors;
a probe base magnetoresistance module located at a
proximal end of the probe shaft wherein the probe
base magnetoresistance module comprises three
orthogonally-oriented probe base magnetoresistance
sensors configured for:
remaining outside the body cavity; and
generating three orthogonal probe base electrical
signals in response to an ambient magnetic field
on said three orthogonally-oriented probe base
magnetoresistance sensors; and
the display is configured to show a horizontal, vertical,
and depth position of the ferromagnetic object relative
to the distal end in a simulated cubic volume in
response to:
the three orthogonal probe tip electrical signals; and
the three orthogonal probe base electrical signals.
17. The ferromagnetic object location visualization sys-
tem as recited in claim 16, wherein:
the three orthogonally-oriented probe tip magnetoresis-
tance sensors and the three orthogonally-oriented probe
base magnetoresistance sensors comprise tunneling
magnetoresistance sensors; and
all tunneling magnetoresistance sensors comprise mag-
netic tunnel junctions comprising two ferromagnetic layers separated by an insulating barrier wherein one of
the ferromagnetic layers has a magnetization that does
not move in response to an applied magnetic field and
the other ferromagnetic layer moves in response to an
applied magnetic field.
18. The ferromagnetic object location visualization sys-
tem as recited in claim 16, wherein:
the system is further configured to detect the ferromag-
netic object in response to a difference in the electrical
signals generated by the probe tip magnetoresistance
module and the probe base magnetoresistance module;
the system is configured to generate an alarm in response
to the ferromagnetic object wherein the alarm is
selected from the group of an audible alarm, a visual
alarm, and a haptic alarm; and
the system is configured for detecting the ferromagnetic
object without generating a magnetic field to detect the
ferromagnetic object.
19. The ferromagnetic object location visualization sys-
tem as recited in claim 16, wherein:
the display comprises a two-dimensional display;
the horizontal and vertical relationship of the ferromag-
netic object is presented as a vertical and horizontal
distance between a probe tip visual marker and a
ferromagnetic object position indicator on the two-
dimensional display; and
the depth position of the ferromagnetic object relative to
the distal end is presented:
as a change in size of the ferromagnetic object position
indicator on the two-dimensional display; and
as a projection of the ferromagnetic object position
indicator onto a base of a simulated cubic volume on
the two-dimensional display.
20. A method for visualizing a location of a ferromagnetic
object in a body cavity of a living organism, the method
comprising the steps of:
establishing a probe shaft that comprises:
a probe tip magnetoresistance module comprising three
orthogonally-oriented magnetoresistance sensors
configured for:
insertion into the body cavity; and
generating three orthogonal probe tip electrical sig-
nals in response to an ambient magnetic field in
three orthogonal axes in the body cavity; and
a probe base magnetoresistance module comprising
three orthogonally-oriented magnetoresistance sen-
sors configured for:
remaining outside the body cavity; and
generating three orthogonal probe base electrical
signals in response to the ambient magnetic field
in three orthogonal axes outside the body cavity;
displaying the relative location of the ferromagnetic
object to the location of the probe tip magnetoresis-
tance module on a two-dimensional display in response
to the three orthogonal probe tip electrical signals and
the three orthogonal probe base electrical signals,
wherein:
the horizontal and vertical position of the detected
ferromagnetic object is presented as a vertical and
horizontal distance between a probe tip visual
marker and a ferromagnetic object position indicator
on the two-dimensional display; and
the relative depth of the detected ferromagnetic object
as compared to the location of the probe tip is
presented using a visual effect selected from the
group of:

a change in size of the ferromagnetic object position indicator on the two-dimensional display; and a projection of the ferromagnetic object position indicator onto the base of a simulated cubic volume on the two-dimensional display.

* * * * *